(12) United States Patent
Meuser et al.

(10) Patent No.: US 8,163,715 B2
(45) Date of Patent: *Apr. 24, 2012

(54) INULIN OF VERY HIGH CHAIN LENGTH

(75) Inventors: Friedrich Meuser, Berlin (DE); Ingo Bauer, Neu-Isenburg (DE); Elke Hellwege, Berlin (DE); Jens Pilling, Dortmund (DE)

(73) Assignee: Bayer CropScience AG, Monheim am Rhein (DE)

( * ) Notice: Subject to any disclaimer, the term of this patent is extended or adjusted under 35 U.S.C. 154(b) by 487 days.

This patent is subject to a terminal disclaimer.

(21) Appl. No.: 12/298,680

(22) PCT Filed: Apr. 27, 2007

(86) PCT No.: PCT/EP2007/004029
§ 371 (c)(1),
(2), (4) Date: Feb. 18, 2009

(87) PCT Pub. No.: WO2007/128560
PCT Pub. Date: Nov. 15, 2007

(65) Prior Publication Data
US 2009/0202705 A1    Aug. 13, 2009

Related U.S. Application Data

(60) Provisional application No. 60/796,819, filed on May 2, 2006, provisional application No. 60/855,250, filed on Oct. 30, 2006.

(30) Foreign Application Priority Data

Apr. 28, 2006  (EP) .................................... 06090064
Oct. 27, 2006  (EP) .................................... 06090200

(51) Int. Cl.
*A61K 31/70*    (2006.01)
*C07H 1/00*     (2006.01)

(52) U.S. Cl. ....................................... 514/54; 536/123.1
(58) Field of Classification Search .................. None
See application file for complete search history.

(56) References Cited

U.S. PATENT DOCUMENTS 1,616,164 A    2/1927    Arsem
1,616,167 A    2/1927    Arsem

FOREIGN PATENT DOCUMENTS

| WO | WO 99/24593   | 5/1999  |
| WO | WO 2006/108697 | 10/2006 |
| WO | WO 2007/128558 | 11/2007 |
| WO | WO 2007/128559 | 11/2007 |

OTHER PUBLICATIONS

Cooper and Carter "Anti-complementary Action of Polymorphic 'Solubility Forms' of Particulate Inulin." Molecular Immunity 23(8): 895-901, 1986.
López-Molina, et al. (Jun. 2005) "Molecular Properties and Prebiotic Effect of Inulin Obtained from Artichoke (*Cynara scolymus* L.)" Phytochemistry 66(12): 1476-1484.
Moerman, et al. (2004) "Enrichment of Higher Molecular Weight Fractions in Inulin." Journal of Agricultural and Food Chemistry 52(12): 3780-3783.
Scott (1931) "Morphological and Chemical Studies on the Globe Artichoke, *Cynara scolymus* L." Proceedings of the American Society for Horticultural Science 27: 356-359.
Wack and Blaschek (2006) "Determination of the structure and degree of polymerisation of fructans from *Echinacea purpurea* roots." Carbohydrate Research 341: 1147-1153.

*Primary Examiner* — Elli Peselev
(74) *Attorney, Agent, or Firm* — Hunton & Williams LLP

(57) ABSTRACT

The invention relates to a long-chain inulin and its preparation from artichoke roots, to its use in foodstuffs and cosmetic preparations and to foodstuffs and cosmetic preparations which comprise the long-chain inulin.

41 Claims, 11 Drawing Sheets

A = washed roots
B = Extract after hot-water extraction

B = Extract after hot-water extraction
C = Precipitated inulin
D = Upper run of the inulin precipitation C = Inulin after precipitation at 4°C
E = Clear phase I after 1st reprecipitation
F = Sedimented inulin after 1st reprecipitation G = Inulin solution after filtration
H = Clear phase III after filtration and inulin precipitation
K = Sedimented inulin after precipitation

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 1
catccggcat taccaccc                                                 18

<210> SEQ ID NO 2
<211> LENGTH: 17
<212> TYPE: DNA
<213> ORGANISM: Artificial Sequence
<220> FEATURE:

```
<223> OTHER INFORMATION: Chemically Synthesized

<400> SEQUENCE: 2
ccaatgtggg ggacctt                                                      17

<210> SEQ ID NO 3
<211> LENGTH: 23
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (6)..(6)
<223> OTHER INFORMATION: y can be t or C

<400> SEQUENCE: 3
tttccytcta attatggcgt att                                               23

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
ggtattagca tctgtttcca                                                   20

<210> SEQ ID NO 5
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 5
ggtcggtctc tcaaccc                                                      17

<210> SEQ ID NO 6
<211> LENGTH: 19
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (13)..(13)
<223> OTHER INFORMATION: r can be g or a

<400> SEQUENCE: 6
gcttcttagt cargtaccg                                                    19
```

INULIN OF VERY HIGH CHAIN LENGTH

CROSS-REFERENCE TO RELATED APPLICATIONS

This application is the U.S. National Stage filing of International Application No. PCT/EP2007/004029, filed Apr. 27, 2007, which claims priority to EP 06090064.4, filed Apr. 28, 2006; U.S. Provisional Patent Application No. 60/796,819, filed May 2, 2006; EP 06090200.4, filed Oct. 27, 2006; and U.S. Provisional Patent Application No. 60/855,250, filed Oct. 30, 2006, the disclosures of each of which are hereby incorporated by reference.

BACKGROUND OF THE INVENTION (i) Field of the Invention

The invention relates to a particularly long-chain inulin and its preparation from artichoke roots, to its use in foodstuffs and cosmetic preparations and to foodstuffs and cosmetic preparations which comprise the particularly long-chain inulin.

(ii) Description of the Related Art

The demand for foodstuffs which contain little fat and more natural raw materials has increased greatly in recent decades. Many substances have already been proposed as substitute for fats, such as products based on carbohydrates or protein or synthetic fat substitutes such as sugar polyesters of fatty acids. However, these always have disadvantages such as a low thermal stability, an unsatisfactory "mouth feel" or an unwanted effect on people or the environment.

It has been known for a long time that inulin is suitable for use in food products. Inulin has a low energy value available for humans and thus use of inulin as fat substitute ensures a large reduction in the calorific value of the final product. In addition, inulin is used as prebiotic addition and bulking agent in foodstuffs.

Inulin is a polysaccharide belonging to the fructan group. It consists of a beta-2-1-linked chain of fructose molecules, and this chain may have an alpha-D-glucose unit at the reducing end. Inulin occurs in economically recoverable amounts in various plants such as, for example, chicory roots, Jerusalem artichoke and dahlia tubers. The average chain lengths of the various inulins and their physicochemical properties differ from plant species to plant species.

The inulins employed to date in the foodstuffs sector are not entirely satisfactory in their processing properties such as, for example, viscosity in aqueous pasty form, thermal stability and stability to acid, emulsifiability and water-binding capacity.

There is in addition a need for inulins with improved fermentation properties and a greater prebiotic effect.

A further problem is that on extraction of inulin with hot water from the plant tissue the extract contains besides the polymer crude inulin also monosaccharides such as glucose and fructose, disaccharides such as sucrose and fructooligosaccharides (DP 3-10). These by-products (mono- and disaccharides, fructooligosaccharides (DP 3-10) may interfere with further processing of the inulin. For example, mono- and disaccharides are undesired in the manufacture of dietetic food products. The sweet taste of the mono- and disaccharides and fructooligosaccharides (DP 3-10) interferes with certain applications in the food products sector. Fructooligosaccharides (DP 3-10) may, because of their hygroscopicity and tackiness, interfere greatly with the use of crude inulin in food products both during processing and during storage. During further processing of the crude inulin, for example by chemical derivatization, mono- and disaccharides and fructooligosaccharides (DP 3-10) may lead to undefined mixtures of products which can be purified only by costly methods or not at all. In addition, a high proportion of reducing sugars has the disadvantage that in thermal processes in the presence of amino compounds there may be unwanted browning reactions, the formation of off-flavors and the production of acrylamide (Maillard reaction).

SUMMARY OF THE INVENTION

The present invention is based on the object of providing an inulin with which it is possible to solve the problems defined above.

The intention was in particular to achieve advantageous processing properties for applications in cosmetics and the foodstuffs industry. Examples thereof are an advantageous viscosity behavior, a high thermal stability and stability to acid, a good emulsifiability and a high water-binding capacity.

One problem addressed by the invention was additionally to provide an inulin having improved fermentation properties and improved prebiotic effect for foodstuffs applications.

Finally, it was desirable to provide an inulin which, by comparison with crude inulin, has a smaller content of mono- and disaccharides and of fructooligosaccharides (DP 3-10).

DETAILED DESCRIPTION OF THE INVENTION

The foregoing problems are solved by the provision of the embodiments defined in the claims.

The present invention relates to an inulin which has an average degree of polymerization $DP_w$ of between 83 and 103, preferably between 84 and 100, more preferably between 83 and 98, even more preferably between 85 and 98, yet more preferably 85 and 95, still more preferably between 86 and 97 and most preferably between 86 and 94.

In this connection and in connection with the present invention, the term "between" is also intended to include the respectively indicated numerical limits.

The term "inulin" is intended to mean in connection with the present invention a polyfructan which consists of a beta-2-1-linked chain of fructose molecules. This chain preferably has at its end a reducing alpha-D-glucose unit.

In connection with the present invention, the term "average degree of polymerization $DP_w$" (average DP weight) means the quotient of the weight-average molecular mass $M_w$, and the molecular mass of the monomer $M_o$. The weight-average molecular mass $M_w$, results from $$M_w = \frac{\sum N_i M_i^2}{\sum N_i M_i},$$

where Ni is the number of molecules with molecular mass Mi.

The "average degree of polymerization $DP_w$" is preferably measured in connection with the present invention by the method of "gel permeation chromatography with light scattering and refractive index detection (GPC-RI-MALLS system)" described hereinafter.

The inulin of the invention exhibits, by comparison with inulins described in the prior art, the surprising advantage that it can be processed to creams which exhibit unusually high stability on heat treatment or acid treatment, so that they are more suitable for example for particular industrial applications or applications in the cosmetics and/or food products industries. In addition, creams comprising the inulin of the invention show an unexpectedly high stability toward shear forces. The inulin of the invention thus exhibits the further advantage, compared with conventional inulin, that it can be processed better in industrial processes in which strong shear forces act.

The inulin of the invention is further notable for particularly advantageous viscosity properties and a high gel strength and a very low solubility, which is advantageous for foodstuffs applications.

In addition, the inulin of the invention shows surprisingly good properties as fat substitute in foodstuffs with excellent sensory properties in the mouth.

The inulin of the invention also shows by comparison with previously employed products a slower fermentation, which is advantageous in the prevention of diseases in the posterior large bowel. The slower fermentation is accompanied by a reduced formation of gas in the bowel, especially of hydrogen.

The inulin of the invention additionally has by comparison with previously employed products a greater prebiotic effect. In particular, the inulin of the invention stimulates the generation of bifidobacteria in an advantageous manner with a simultaneous reduction of unwanted and/or pathogenic bacteria. The inulin of the invention is therefore suitable for use in foodstuffs and/or medicaments for the prevention and treatment of bowel dysfunctions and diseases, especially in the posterior large bowel.

Finally, the inulin of the invention also confers on various foodstuffs advantageous use properties such as, for example, viscosity increase, emulsifiability, water-binding capacity and crumb formation. The inulin of the invention surprisingly confers improved baking properties on bakery products and increases the dough yield. The inulin of the invention is moreover an effective means for flavor modification and foam stabilization.

In a further embodiment, the inulin of the invention has a content of fructooligosaccharides (oligofructans) having a DP of from 3 to 10 which is less than 3%, preferably less than 1.5%, particularly preferably less than 0.7%, very particularly preferably less than 0.3%.

In a further embodiment, the inulin of the invention has a glucose content of less than 2%, preferably less than 1%, particularly preferably less than 0.5%, very particularly preferably less than 0.2% and most preferably less than 0.1%.

In a further embodiment, the inulin of the invention has a fructose content of less than 2.5%, preferably less than 1.5%, particularly preferably less than 1.0%, very particularly preferably less than 0.3% and most preferably less than 0.15%.

In a further embodiment, the inulin of the invention has a sucrose content of less than 2%, preferably less than 1%, particularly preferably less than 0.5%, very particularly preferably less than 0.3% and most preferably less than 0.1%.

In an embodiment of the inulin of the invention which is particularly advantageous for foodstuffs applications, the content of mono- and disaccharides is less than 0.5%.

All percentages are, unless otherwise indicated, percent by weight based on the total dry weight of inulin and further substances. "Further substances" are all substances in the dry mixture which are different from inulin.

The fructose, glucose and sucrose content is measured in connection with the present invention by the optical enzymatic method described below (general methods: "sugar determination").

In a further embodiment, which may include the previous embodiments, the inulin of the invention has a weight average molecular mass $M_w$, of between 13 400 g/mol and 16 700 g/mol, preferably between 13 600 and 16 200 g/mol, more preferably between 13 750 g/mol and 15 900 g/mol, and particularly preferably between 13 900 g/mol and 15 750 g/mol and most preferably between 13 900 g/mol and 15 250 g/mol.

The weight-average molecular mass $M_w$ is preferably measured in connection with the present invention by the method of "gel permeation chromatography with light scattering and refractive index detection (GPC-RI-MALLS system)" described hereinafter.

In a further embodiment, which may include the previous embodiments, the inulin of the invention has an average degree of polymerization $DP_{n\ (GPC)}$ measured by gel permeation chromatography (GPC) of between 66 and 89, preferably between 68 and 85, particularly preferably between 70 and 85 and even more preferably between 72 and 84.

The "average degree of polymerization $DP_n$" is measured in connection with the present invention preferably by the method of "gel permeation chromatography with light scattering and refractive index detection (GPC-RI-MALLS system)" described hereinafter.

In connection with the present invention, the term "average degree of polymerization $DP_n$" (mean DP number) means the quotient of the number-average molecular mass $M_n$ and the molecular mass of the bound monomer $M_o$ (anhydrofructose=162 g/mol). The number-average molecular mass results from $$M_n = \frac{\sum N_i M_i}{\sum N_i},$$

where Ni is the number of molecules having molecular mass $M_i$.

In a further embodiment, which may include the previous embodiments, the inulin of the invention has a molecular weight distribution in the range from 650 to 48 000, more preferably 970 to 40 000 g/mol, even more preferably 1300 g/mol to 34 000 g/mol and most preferably from 4000 g/mol to 26 800 g/mol.

In yet a further embodiment, which may include the previous embodiments, the inulin of the invention shows a total mass of inulin molecules having a molecular weight of <10 000 g/mol based on the total mass of all inulin molecules of 20-36% and a total mass of inulin molecules having a molecular weight of >20 000 g/mol based on the total mass of all inulin molecules of 7-23%. It is even more preferred for the total mass of inulin molecules having a molecular weight of <10 000 g/mol based on the total mass of all inulin molecules to be 25-31% and the total mass of inulin molecules having a molecular weight of >20 000 g/mol based on the total mass of all inulin molecules to be 12-18%.

The molecular weight distribution is preferably measured in connection with the present invention by the method of "gel permeation chromatography with light scattering and refractive index detection (GPC-RI-MALLS system)" described hereinafter.

In one embodiment of the inulin of the invention with particularly advantageous properties, the degree of branching, measured as the proportion of beta 2,6 linked fructose units, is 0.5-2.0 mol %, more preferably 0.7-2.0 mol %, even more preferably 0.9 to 2.0 mol % and most preferably 1.1 to 2.0 mol %. The degree of branching is defined herein as the percentage number of beta-2-1-linked fructose monomers with additional branch point at position 6 of the fructose monomer (also abbreviated to "2-1,6-" hereinafter) based on the total number of all inulin monomers measured in a sample of the inulin of the invention with randomly distributed molecular weights. At its position 6, a "2-1,6-" fructose monomer within a polyfructose chain is linked to another polyfructose chain, consisting of at least two beta-2-1-linked fructose monomers, or to a single fructose monomer. The term "branch point" designates a position of a fructose monomer, within a polyfructose chain, to which another polyfructose chain consisting of at least two beta-2-1-linked fructose monomers, or a single fructose monomer is linked. The degree of branching is measured by the method of standard methylation analysis or alternatively by the method of reductive degradation after methylation. Both methods are described in detail in the appended examples.

An embodiment of the inulin of the invention which is particularly advantageous in its properties and which may include the previously described embodiments has a particularly narrow molecular weight distribution expressed by the quotient between the weight average degree of polymerization and the number average degree of polymerization DPw/DPn. This quantity is also referred to as polydispersity index. In a preferred embodiment, the quotient DPw/DPn is less than 1.25, in a more preferred embodiment is less than 1.20, in an even more preferred embodiment is less than 1.15 and in the most preferred embodiment is less than 1.10. The values for DPw and DPn are in this connection measured by the method of "gel permeation chromatography with light scattering and refractive index detection (GPC-RI-MALLS system)" described hereinafter. The molecular weight of a monomer for conversion calculations is set equal to 162 g/mol.

The invention further relates to an aqueous paste of the inulin of the invention which is obtainable by dispersing the inulin in water, shearing the resulting dispersion until homogeneous, storing the product obtained in this way at 4-15° C. for 12-24 h and, after conditioning to room temperature, stirring to give a homogeneous paste. A preferred paste comprises water and 1-40% by weight, more preferably 1-35% by weight, still more preferably 1-30% by weight, even more preferably 2-25% by weight, yet more preferably 2-20% by weight, and particularly preferably 10-20% by weight inulin based on the total weight of the paste. The term "paste" is according to this invention equivalent to a suspension of cristalline and/or amorphous inulin. Accordingly, the term "aqueous paste" is to be understood as a suspension of cristalline and/or amorphous inulin in aqueous phase. The aqueous phase is based on water which can optionally comprise further dissolved or suspended substances, such as salts, other carbohydrates, proteins, amino acids. In an advantageous embodiment the inulin in the paste is a spray dried inulin, i.e. an inulin which was spray dried before forming the paste.

The above described paste can be used as a component in aqueous systems. Preferred aqueous systems are foodstuffs on aqueous basis and cosmetics, wherein the term "foodstuff" is defined elsewhere in the present description. Examples of preferred foodstuffs are also listed elsewhere in the present description. In foodstuffs and cosmetics, a paste according to the invention can be used as structure imparting component, thickening agent, texturizing agent, stability enhancing agent or viscosity-building agent, wherein the paste in this connection can fulfil one or more of the above mentioned functions. In foodstuffs, a paste according to the invention can also be used as a fat substitute, oil substitute, prebiotic agent and/or dietary fiber component, wherein the paste in this connection can fulfil one or more of the above mentioned functions. The most preferred use is the use as an oil or fat substitute. The most preferred foodstuffs wherein a paste according to the invention is used as a component, are dairy products, such as yoghurt, yoghurt drinks, cream, crème fraiche, curd, butter, milk, especially skim milk, buttermilk, soured milk, kefir, cheese, such as cream cheese, soft cheese, sliced cheese, hard cheese, whey, milk powder, drinks on milk basis.

The inulin of the invention shows a surprisingly high stability to acid. In particular, an aqueous paste of the inulin of the invention shows a high stability to acid. The shear stability of an aqueous inulin paste of the invention is likewise exceptional by comparison with commercially available products.

The inulin of the invention is distinguished from other, commercially available inulins by a surprisingly high gel strength. Gel strengths of 4-100 N, more advantageously 10-100 N, even more advantageously 20-100 N and most advantageously 40-100 N, are achieved at a concentration of 1-35%(w/w), more preferably 1-30% (w/w), still more preferably 2-25% (w/w), yet more preferably 2-20% (w/w), most preferably about 20% (w/w) of the inulin of the invention in water when inulin is dissolved at 90° C. and then stored at room temperature (23° C.) for a period of 24 h. High gel strengths as indicated previously can be attained particularly well with inulins of the invention which are spray dried and then employed for gel formation. The gels obtained in this way preferably show a particulate character (particle gels). The measurement method for determining the gel strength is described in detail in the examples section (structure formation by inulins after heating in water).

The present invention relates in a further aspect to a process for obtaining inulin in which
a) artichoke roots are comminuted
b) an extract is obtained by treating the comminuted roots with water,
c) coloring constituents are removed from the extract obtained,
d) inulin is precipitated from the extract,
e) the inulin is reprecipitated at least once.

The process is particularly suitable for obtaining the previously described inulins of the invention, but is not restricted thereto.

Artichoke roots are used as starting material, but the process is not restricted to a particular variety. The comminution is advantageously preceded by removing any adherent contaminants from the roots, e.g. by vigorous washing with water with a high-pressure cleaner. It is advantageously possible to wash the roots in the deep-frozen state in order to minimize the loss of mass of root material.

If necessary, the roots are initially comminuted coarsely, e.g. by chopping. Shredders are preferred for the further comminution. The product obtained is comminuted root material in the form of fibrous chips.

In the most advantageous embodiment of the process, artichoke roots with the following characteristics are used: ripe roots with respect to the formation of dry mass and inulin. The degree of ripeness can be established from the ratio of inulin content to dry matter content and the ratio of fructose content to inulin content. The inulin content is preferably in the range of 30-70% by weight, more preferably 40-65% by weight, still more preferably 50-60% by weight, based on total weight of dry matter of roots, and the fructose/inulin ratio is preferably in the range of 3-24% by weight, more preferably 3-12% by weight, most preferably lower than 6% by weight. The dry matter content of the cleaned artichoke roots is preferably 20-50% by weight, more preferably 30-40% by weight, more preferably 30-35% by weight, based on the total weight of cleaned roots.

In case that artichoke roots must be stored before using them in the process of the present invention, the roots should be conserved in order to prevent microbial contamination, rotting or decrease of molecular weight of inulin due to enzymatic degradation. Preferred methods for conservation of the roots are freezing or hot air drying of comminuted roots for storage.

After the comminution, the comminuted root material is extracted with water, preferably at a temperature of 60° C. to 95° C., most preferably 80-95° C. The extraction preferably takes place in the neutral to slightly alkaline pH range. A temperature of at least 60° C. at pH 7-9 is advantageous because in this case enzymatic and acidic hydrolysis is suppressed. The concentration of comminuted root material in the water is preferably 10-40% by weight, more preferably 20-30% by weight, measured as fresh weight of roots based on the total weight of the extraction mixture.

Preferably a ratio between the dry matter of the shredded material used and the water as extraction medium is established which leads to a dry matter content in the extract of 8-12% by weight and an inulin content of more than 6% by weight, preferably 6-8% by weight, based on the weight of the extract. A correspondingly suitable choice of extraction conditions, such as the ratio of water to root weight, can lead to a transfer of 80-90% by weight of the inulin present in the roots into the extract. The aforementioned conditions are suitable to achieve a favorable crystallization and a high yield of the inulin from the extract, based on the observation that the high molecular weight inulin crystallizes from the extract even at a concentration as low as 5% by weight, based on the weight of the extract.

There is no special restriction on the extraction equipment, and conventional extraction techniques for plant material can be applied. It is most preferred according to the invention for the extraction to take place in a jacket-heated extractor with agitator. In another highly preferred embodiment a heatable lauter tun is used as stirred extractor. Thus, the extraction of the inulin from the roots is combined with the separation of the extract from the spent chips by filtration, as described below. The extraction time after equilibration of the root/water mixture is preferably 30 min-4 hours, preferably 1-2 hours. After this time, the extract is separated from the spent chips, e.g. by pumping off or straining off or filtration.

After separation of the extract from the spent chips, where appropriate, fibrous materials and plant fragments may remain as suspended materials in the extract. If present, these suspended materials are likewise removed from the extract. In this variant of the process, step b) of the process is thus followed, before step c), by a step in which suspended materials, mainly consisting of fibers, are removed from the extract. The acceptable amount of suspended materials and whether removal is to take place will be decided by the skilled worker from case to case. Removal of the suspended materials can take place by conventional separation techniques, as centrifugation or filtration. A desludging separator has proved particularly suitable. A screen or filter with appropriate fineness can also be used.

In a highly preferred embodiment, the suspended material can be filtered off by using the spent chips as a filter material. In this embodiment the spent chips are precipitated at the bottom of the extraction vessel equipped with a sieve at the bottom, like a lauter tun. The sieve is preferably a slit sieve. The precipitated spent chips are used as a filtration bed through which the extract flows. By using this technique a nearly quantitative removal of suspended material is possible without using further filtration steps before further refining or brightening the extract or crystallizing the inulin.

The extracts are colored owing to their content of coloring constituents and colloidally suspended colorized matter. The coloring constituents consist, inter alia, of tannins and flavanoids and usually confer a yellow or brownish yellow and/or dark brownish color on the extract. The inulins which can be obtained directly from such extracts do not comply with the desired requirements concerning a neutral color. It is therefore necessary to remove the coloring constituents from the extract in step c) of the process. Process step c) of the invention for removing coloring constituents from plant extracts is generally also referred to as decolorization, clarification or "brightening" of plant extracts. These terms are equivalent in the context of the present invention.

The brightening can take place according to the invention by adding lime and subsequent carbonation ($CO_2$ addition). The process of lime addition is known from the prior art and is used for example in obtaining sucrose from sugar beet. In an alternative brightening process, the interfering constituents are removed using an ion exchanger.

In a particularly advantageous embodiment of the process, the coloring constituents are removed in step c) by
i) admixing magnesium ions ($Mg^{2+}$) to the plant extract,
ii) admixing at least one alkaline component to the plant extract,
iii) forming a precipitate, and
iv) removing the precipitate which has formed from the plant extract.

Steps i)-iv) in this particularly preferred variant are sub-steps of process step c).

This process variant surprisingly makes more effective decolorization of the extract possible compared with the lime brightening process. In addition, the auxiliaries employed, magnesium salts and alkalis, are low-cost. The process is thus less costly than the use of an ion exchanger. The expenditure on apparatus and time for carrying out this process step is also particularly low. Finally, this type of brightening also simultaneously removes materials causing turbidity from the extract.

Magnesium ions (Me) are admixed according to the invention to the aqueous plant extract. It is possible in a variant of step i) to add an aqueous solution of a magnesium salt to the plant extract. In a further, more preferred variant, a magnesium salt is added directly in solid form to the plant extract and dissolved therein.

If a magnesium salt is added, it is preferably a salt which, owing to its high solubility product, is very readily soluble in water. Particularly suitable magnesium salts are selected from magnesium chloride, magnesium sulfate, magnesium nitrate, magnesium salts of lower fatty acids such as magnesium acetate and propionate, and mixtures thereof.

An alkaline component in means according to the invention a component which comprises hydroxide ions (OH) or forms hydroxide ions in the extract after combining with the plant extract. The alkaline component may be liquid, solid or gaseous. A liquid alkaline component is preferably employed.

On addition of magnesium ions and an alkaline component as described in steps i) and ii) of the process, a precipitate is formed by a precipitation reaction. Steps i) and ii) can in the context of the present process in principle be carried out simultaneously, especially if a solution of magnesium ions is used in step i) and an alkaline liquid is used in step ii). However, it is preferred to carry out process step i) first and then step ii).

It is advantageous for process step c) that both the magnesium ions and the alkaline component are distributed as homogeneously as possible in the extract so that the precipitation reaction in the extract is also homogeneous and as quantitative as possible. It is therefore preferred to employ as alkaline component aqueous alkaline liquids such as, for example, alkaline solutions or alkaline suspensions which can be rapidly and homogeneously mixed into the plant extract. An alkaline solution or suspension comprises according to the invention hydroxide ions (OH⁻) or forms them after combining with the plant extract.

In a very preferred process variant, a magnesium salt is homogeneously dissolved in the extract first in step i). Subsequently, in step ii), an aqueous alkaline solution or suspension is added.

In one embodiment, the alkaline component is an aqueous solution or suspension of an alkali metal or alkaline earth metal hydroxide. The hydroxide is preferably selected from the hydroxides of the alkali metals and alkaline earth metals, such as lithium hydroxide, sodium hydroxide, potassium hydroxide, calcium hydroxide and barium hydroxide.

In a very particularly preferred variant, the alkaline component is a suspension of calcium hydroxide. The advantage of using calcium hydroxide is that a particularly small amount of centrifugate is obtained in step iii). In addition, the simultaneous precipitation of magnesium hydroxide and calcium sulfate achieves a greater sedimentation rate and a greater compressibility of the precipitate. The precipitate has particularly little gelatinous consistency. The binding of inulin in the precipitate thus remains particularly low in this process variant.

A further alkaline component which can be used is ammonia, preferably in aqueous solution. Nor is it excluded in principle to use gaseous ammonia, but this is less preferred than the use of an aqueous solution.

In a further embodiment, the alkaline component is an aqueous solution or suspension of an organic base such as ethylenediamine and triethanolamine.

Salts of weak organic acids such as alkali metal and alkaline earth metal acetates, especially sodium acetate, potassium acetate, calcium acetate and magnesium acetate, can also be used.

Magnesium hydroxide is formed as precipitate. The coloring constituents of the aqueous extract remain according to the invention in the precipitate and are thus separated from the liquid phase. A substantially decolorized extract is obtained. The amounts of $Mg^{2+}$ ions and alkaline component employed, and thus the amount of precipitate formed, determine inter alia how quantitative the decolorization is. Optimization of the amounts of the reactants is within the competence of a skilled worker. In case of magnesium sulfate, the preferable concentration is in the range of 0.5-3% by weight, more preferably 0.5-2% by weight of the aqueous extract.

In the preferred variant of step c), as described above, the molar ratio of hydroxide ions to magnesium ions $OH^-:Mg^{2+}$ is preferably from 2.2:1 to 1.8:1. It is most preferred for the ratio to be exactly stoichiometric, i.e. $OH^-:Mg^{2+}=2:1$. The amount of alkaline component is thus to be chosen so that the appropriate amount of hydroxide ions is present for the magnesium ions.

The dissolving of the magnesium salt and admixing of the alkaline component in process steps i) and preferably takes place with stirring in order to achieve dissolution and homogenization as quickly as possible and thus a fast reaction. However, there are no particular further restrictions on the mixing technique. Thus, the process can be carried out for example also by other mixing techniques familiar to the skilled worker.

To expedite the process, step i) is preferably carried out at a temperature of 60-80° C. The reaction time after addition of the alkaline component is generally from about 1 to 15 min, averaging about 10 min.

The removal step iv) preferably takes place by sedimentation or filtration. The sedimentation can be made faster by a centrifuge, preferably a disk centrifuge, in particular a desludging centrifuge. However, other separation techniques familiar to the skilled worker can also be used. These can also be carried out in combination with one another, e.g. centrifugal desludging of the brightened extract with subsequent filtration of the desludged extract, e.g. with a plate filter.

The whole of step c) of the process of the invention may if required also be carried out more than once. If the previously described preferred variant of step c) with substeps i)-iv) is used, it is also possible for the individual substeps i)-iv) to be carried out more than once.

After step c), inulin is precipitated from the extract in step d). The precipitation can be effected for example by adding alcohols such as ethanol, methanol or isopropanol. In this case, depending on the amount of alcohol added or adjusted polarity of the liquid phase, initially high molecular weight inulin fractions are precipitated, so that it is possible to influence, via the amount of alcohol added, how quantitatively the inulin present in the extract is precipitated and which molecular weight fractions are predominantly obtained. Besides alcohol, it is also possible to employ other nonpolar organic liquids which are miscible with water.

For this purpose, in a particularly advantageous embodiment of this process step, to limit the use of alcohol, especially ethanol and isopropanol, the prepared extract is initially concentrated, preferably to one fourth to one fifth of its initial volume. The concentration can take place by evaporation or membrane filtration and a combination of both processes. Care must be taken in this case that the concentrate is kept hot during the concentration, preferably at 60-95° C., in order to avoid precipitation of the inulin. An advantage of membrane filtration is the depletion, associated therewith, in low molecular weight substances accompanying the inulin. The subsequent precipitation of the inulin from the concentrate can be managed by the choice of increasing alcohol concentration so that the inulin is fractionated according to molecular size ranges which are characterized for example by the weight average degree of polymerization (DPw). Depending on the choice of the precipitation conditions, the result is fractions which have the DPw according to the invention. Depending on the desired purity.

It is more preferred to obtain inulin by cooling the extract than by alcoholic precipitation. The preferred conditions are such that the extract is cooled to a temperature of 2-10° C., more preferably 2-8° C. and kept at this temperature over a period of from 6 to 140 h, preferably 6 to 48 h, during which the inulin precipitates. The cooling rate and temperature, and the duration of the cooling influence the precipitation of the inulin from the extract and the breadth of the molecular weight distribution and thus at the same time the quantity. Choice of a longer period and lower temperature results in precipitation of more low molecular weight inulins and a broader molecular weight distribution and thus a lower average molecular weight of the precipitated fraction. The precipitated inulin is separated from the liquid phase by conventional separation techniques such as, for example, centrifugation, decantation, filtration.

In a preferred embodiment, inulin is crystallized for the first time after the extraction step b) and before step c) of the above described process. Such crystallisation is preferably done as described previously. Crystallisation before step c) leads to an increase in the yield of high molecular weight inulin compared with direct brightening of the extract, and economizes the use of the brightening agents, i.e. magnesium compound and the alkaline component. It is advantageous to brighten the extract after the first crystallisation of the inulin as in this case only the coloring constituents bound to the inulin crystals have to be removed, which leads to a similarly smaller amount of inulin bound to the brightening sludge.

A first precipitation and removal of the precipitated inulin can be followed by renewed cooling of the extract or addition of alcohol in order to obtain any inulin fractions which are still dissolved. A decision about repetition is made from case to case according to how quantitatively the inulin is to be obtained from the plants and what molecular weight distribution in the final product is desired.

The inulin concentration in the extract depends substantially on the inulin content of the roots and the concentration of the comminuted roots in the extract and is a further variable which has an effect on the precipitation of the inulin by cooling the extract. The dependence of the precipitation on the concentration can therefore be utilized in order to concentrate the liquid phase after the first precipitation, e.g. by evaporation, in order also to precipitate the low molecular weight fractions if this is desired.

In the last process step c), the precipitated inulin is reprecipitated. "Reprecipitation" means in the context of this invention that the solid inulin, resulting from the previous process step, is redissolved and then precipitated and/or crystallized out of the solution again. Thus, process step c) can also be worded as: the inulin is dissolved and precipitated and/or crystallized again, wherein this step is done at least once. The crystallization differs from the precipitation in that predominantly crystalline structures are obtained.

The inulin is preferably dissolved under the influence of heat and preferably in water. Water with a temperature of 70-100° C., in particular 90-100° C., is particularly suitable.

The precipitation in step e) can take place by alcoholic precipitation as previously described. However, the inulin is preferably obtained by cooling the solution to 2-10° C., more preferably 2-8° C. over a period of 6 to 140 h, preferably 12-48 h.

The precipitation of the inulin dissolved in step e) can be repeated in order to obtain the inulin still remaining in the liquid phase. A decision about repetition is to be made from case to case according to how quantitatively the inulin is to be obtained from the plants and what molecular weight distribution in the final product is desired. The liquid phase can be concentrated in order to simplify the precipitation.

After reprecipitation, the resulting inulin solid is separated from the liquid phase by conventional separation techniques such as, for example, centrifugation, decantation, filtration.

In order to influence the molecular mass distribution and purity of the resulting inulin product, process step e) can be carried out more than once. It has emerged that the averages of the molecular weight and the averages of the degree of polymerization are shifted to higher values on repetition of the reprecipitation step e). It is thus possible to set various averages of the molecular weight/degree of polymerization of the inulin of the invention within the claimed range.

If fine-particle impurities are still present, it is advantageous to insert one or more filtration steps into the process. Any fine-particle impurities present are removed in the filtration. The fineness of the filter is chosen by the skilled worker depending on the particle size of the impurity.

The filtration step(s) can be inserted anywhere in the process after obtaining the extract. A filtration step directly after obtaining the extract in step b) for example is advantageous. The filtration step is to be distinguished from the removal of suspended materials as described previously, because the particles removed by the filtration are finer than the suspended materials, which consist mainly of fibers. In a further preferred embodiment, the filtration step is carried out before step d).

The filtration step is preferably combined with a reprecipitation as described for process step c). This entails the inulin being dissolved as previously described for step e), and the solution then being filtered. After the filtration, the inulin is precipitated or crystallized out of the filtered solution. The solid inulin resulting after the precipitation or crystallization can be separated from the liquid phase by conventional separation techniques, such as, for example, centrifugation, decantation and filtration.

In some cases the resulting inulin can be discolored by substances which can not be removed by filtration. In such cases it is preferred to remove the coloring impurities by a treatment with activated carbon. In one embodiment active charcoal is suspended in water and added to an inulin solution at a temperature of above 80° C., preferably above 90° C. In case of a 20% by weight inulin solution the amount of active carbon is preferably in a range of 1-10% by weight, preferably 2-6% by weight, more preferably 2-3% by weight, based on the weight of the inulin solution. After adsorption of the coloring impurities, the activated carbon is removed by centrifugation and/or filtration. The activated-carbon suspension can be preclarified by centrifugal separation of the activated-carbon sludge and then clarified by two-stage filtration, for example with a combination of a kieselguhr precoat filter and a sheet filter. It is important that during the separation of the active charcoal from the inulin solution the temperature is maintained above 80° C., preferably above 90° C., in order to keep the inulin in solution. After removal of the active charcoal, the inulin can be precipitated or crystallized and separated from the liquid phase as described above.

After separation from the liquid phase, the final product can be washed again with water or a water/alcohol mixture. Washing with cold water at a temperature of 2-10° C. is preferred. For this purpose, the inulin precipitate is slurried in water and the inulin is then sedimented again.

The resulting inulin is preferably dried in a further, last process step. The drying can take place by freeze drying, spray drying or drum drying.

In a preferred embodiment, the inulin of the invention is in spray-dried form. Suitable spray-drying parameters are described in the appended examples. It is self evident that in case of a spray drying process a precipitated or crystallized inulin must be brought into suspension (in water below about 80° C.) or into solution (in water above about 80° C.) again. Alternatively, a last precipitation or crystallization step, as described above, can be omitted and the suspended or dissolved inulin from the process can directly be spray dried. It is possible by adding spray-dried inulins of the invention to liquid prepared food products for the viscosity to be increased particularly effectively. On addition of equal quantities of inulin of the invention, a greater increase in viscosity is achieved with a spray-dried inulin compared with an inulin dried in another way (e.g. freeze drying).

In yet a further preferred embodiment, the inulin of the invention is in spray-granulated form. Spray-granulated inulin is obtained by known processes, e.g. by introducing a previously spray-dried material as granulation seed and spray drying further inulin. An inulin with a particle size of 10-100 µm for example can serve as initial charge. Suitable spray-granulation conditions are for example a feed composition of 70% water and 30% inulin and a feed temperature of 90° C.

The inulin of the invention very particularly preferably has an average particle diameter of 50-350 µm, more preferably 80-300 μm, even more preferably 100-250 μm and most preferably 100-200 μm. Such an inulin is thus a further aspect of this invention.

The average particle diameter can be determined both by sieve analysis of a dry sample and by light scattering. The preferred method is, however, sieve analysis so that the inulin of the invention preferably has an average particle diameter of 50-350 μm, more preferably 80-300 μm, even more preferably 100-250 μm and most preferably 100-200 μm, determined by sieve analysis.

In one embodiment, the inulin of the invention having the described particle sizes is obtained by spray-drying or spray-granulation process. A spray-dried or spray-granulated inulin having the previously described particle sizes is thus a further aspect of this invention.

It is possible to adjust the preferred average particle diameter of a dried inulin by means of sieve fractionation in the event that, after drying, it is still outside the preferred range. Selection of the suitable sieve size lies within the competence of the average skilled worker.

The inulin particles of the invention preferably have a crystalline fraction of less than 45%, more preferably less than 40%, even more preferably less than 35%. In a further preferred embodiment, less than 20%, even more preferably less than 10%. In the most preferred embodiment, the degree of crystallinity is less than 1%. The stated degrees of crystallinity are determined by the method of Ruland-Vonk (W. Ruland, Acta Cryst., 14, 1180 (1961); C. G. Vonk, J. Appl. Cryst. 6, 148 (1973)). The method for determining the degree of crystallinity is described in detail in the appended examples. A low degree of crystallinity confers better dissolving properties on the inulin, which is advantageous in certain foodstuff applications.

In yet a further aspect, the invention also relates to compositions which comprise the previously described inulin of the invention and one or more edible or pharmaceutically acceptable ingredients. Typical compositions include foodstuffs for humans and animals, beverages, functional foodstuffs, medicaments and pharmaceutical compositions (including prophylactic compositions and therapeutic compositions), and intermediates thereof.

A functional foodstuff means in the context of the present invention a foodstuff which apart from traditional nutrients comprises an ingredient which may have a health-promoting effect (definition of the Institute of Medicine of the National Academy of Sciences, USA, 1994).

Said edible or pharmaceutically acceptable ingredients are preferably selected from the group consisting of sugars (e.g. glucose, fructose, sucrose, lactose, galactose, maltose, isomaltose, polydextrose), polyols (e.g. sorbitol, lactitol, maltitol, isomalt, mannitol, xylitol), maltodextrins, sweeteners, hydrogenated glucose syrups, additions to human and animal foods, intermediates for human and animal foods, human and animal food products, edible liquids, beverages, bioavailable sources of minerals, pharmaceutically acceptable carriers, pharmaceutically and therapeutically active substances, pharmaceutical compositions and medicaments.

A particularly preferred composition of the present invention includes the inulin of the invention in the presence of an edible or pharmaceutically acceptable, bioavailable source of minerals, especially a source of calcium and/or magnesium and/or iron, such as, for example, dairy products and salts and complexes of calcium, magnesium and iron.

As explained above, the aim of the present invention was to provide an inulin with particularly advantageous properties for use in foodstuffs, with the terms food product and foodstuffs being equivalent according to the invention. In a further aspect, the present invention thus also relates to foodstuffs and dietary supplements which comprise the previously described inulin. The terms foodstuffs include according to the present invention both foodstuffs for humans and animal foodstuffs or animal feed. The dietary supplements include dietary supplements for humans and for animals.

A particularly preferred foodstuff is selected from dairy products, yoghurts, ice creams, milk-based soft ice, milk-based garnishes, puddings, milkshakes, egg custard, cheese, nutrition bars, energy bars, breakfast bars, confectionery, bakery products, crackers, cookies, biscuits, cereal chips, snack products, ice tea, soft ice made from fruit juice, diet drinks, finished drinks, sports drinks, stamina drinks, powdered drink mixtures for dietary supplementation, infant and baby food, calcium-supplemented orange juice, bread, croissants, breakfast cereals, noodles, spreads, sugar-free biscuits and chocolates, calcium chews, meat products, mayonnaise, salad dressings, nut butter, deep-frozen meals, sauces, soups and ready-to-serve meals. The foodstuff comprising the inulin of the invention is most preferably a dairy product, especially a yoghurt. The inulin of the invention shows a particularly good effect on the stability, the texture, the body and the mouth feel of dairy products, especially yoghurt, possibilities being stirred or pot-fermented yoghurt or yoghurt drinks.

Other useful dairy products according to the present invention are cream, crème fraiche, curd, butter, milk, especially skim milk, buttermilk, soured milk, kefir, cheese, such as cream cheese, soft cheese, sliced cheese, hard cheese, whey, milk powder, drinks on milk basis.

A preferred level of inulin in foodstuffs, especially in dairy, particularly in yoghurt, is 0.2-5% by weight, preferably 0.5-4.5% by weight of dry inulin, based on the total weight of all components of the foodstuff, dairy, or yoghurt.

In one embodiment of the invention, the foodstuff is a foodstuff manufactured by an extrusion process, such as, for example, a breakfast cereal.

In a further aspect, the present invention relates to cosmetic preparations which comprise the previously described inulin. The cosmetic preparation particularly preferably takes the form of creams, in particular skin and face creams.

In a further aspect, the present invention also relates to the use of the previously described inulin as addition in foodstuffs, functional foodstuffs and cosmetic preparations. The use also relates in particular to all specific foodstuffs and cosmetic preparations as mentioned above.

In yet a further aspect, the present invention relates to the use of the inulin of the invention for the manufacture of a pharmaceutical composition or of a medicament.

The inulin of the invention can advantageously be used in foodstuffs, functional foodstuffs, pharmaceutical compositions or medicaments which serve to modify or regulate the composition of the bacterial flora in the large bowel, especially in the distal region of the large bowel, of humans, mammals and other vertebrates.

It is likewise possible to use the inulin of the invention in foodstuffs, functional foodstuffs, pharmaceutical compositions or in medicaments which serve to modify or regulate the fermentation pattern of inulin in the large bowel, especially in the distal region of the large bowel, of humans, mammals and other vertebrates.

A further preferred use of the inulin of the invention is the use as fat or oil substitute and/or as a dietary fiber in foodstuffs, wherein the term "foodstuff" encompasses at least all above mentioned foodstuffs, especially all above mentioned dairy products. It is advantageous that the sensory properties, especially the mouthfeel, are excellent compared with conventional inulins. Thus, inulin of the present invention can also be used as an enhancer of sensory properties, especially as a mouthfeel enhancer, in foodstuffs.

A further use of inulin of the invention is the use as a texturizing agent, stability enhancing agent, viscosity-building agent, especially in foodstuffs and cosmetics. The term "foodstuff" encompasses at least all above mentioned foodstuffs, especially all above mentioned dairy products.

Finally, the inulin of the invention can be used in foodstuffs, functional foodstuffs, pharmaceutical compositions or in medicaments which have the following advantageous effects: roughage effects, regulation of bowel function, prebiotic effect and/or bifidogenicity, increased absorption of minerals, e.g. of calcium, magnesium and iron, increase in bone mineral density, increase in the bone mineral content, increase in the maximum bone mass, improvement in bone structure, reduction in the loss of bone mineral density, reduction in the loss of bone structure, regulation of lipid metabolism, stimulation of the immune system, prevention of cancer and reduction of the risk of cancer, prevention of large bowel cancer and reduction of the risk of large bowel cancer and prevention of breast cancer.

Figure 1:
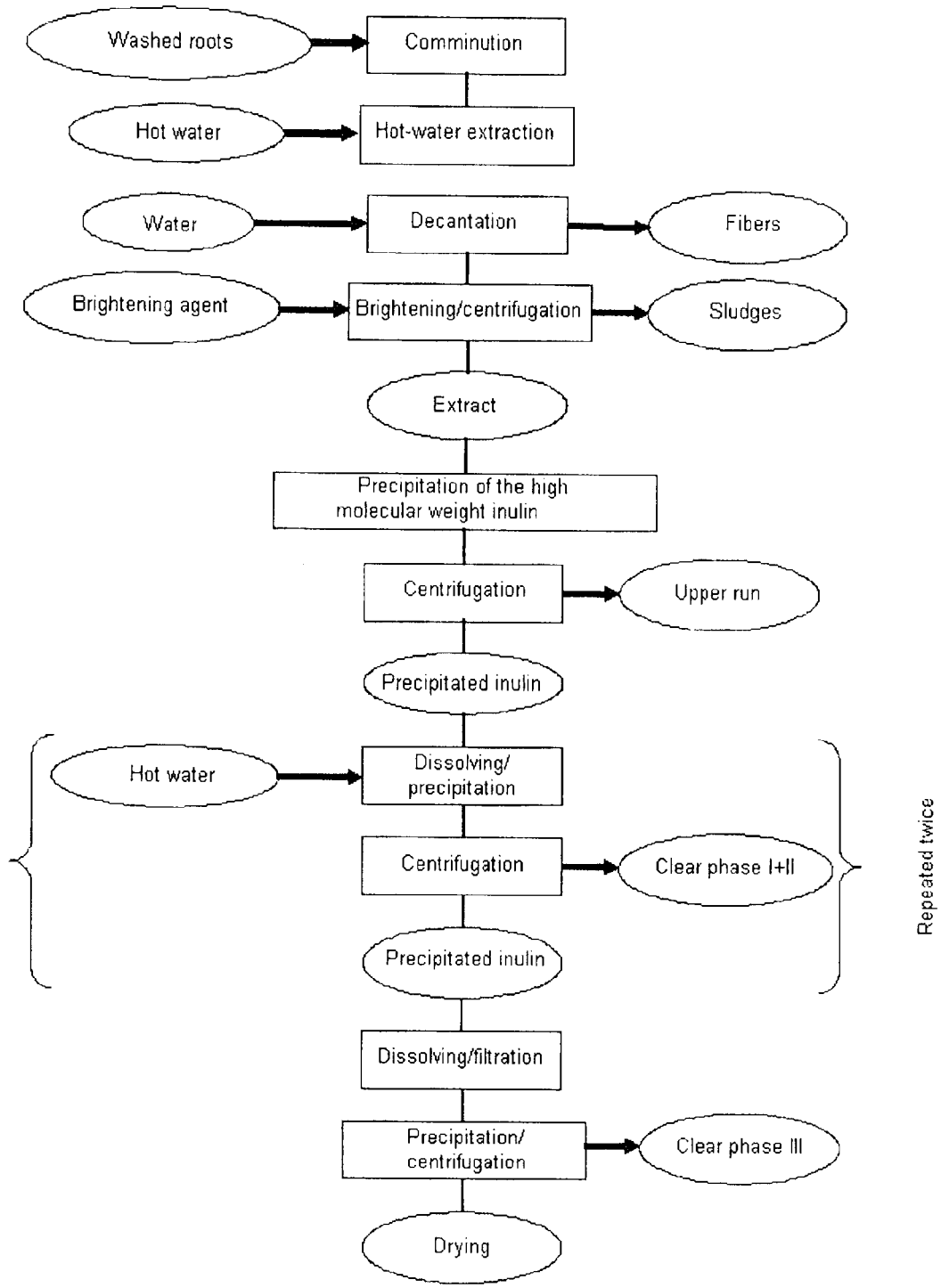
FIG. 1 shows a diagrammatic representation of the progress of inulin extraction.

The invention is explained below by means of examples which are not intended to restrict the general inventive concept.

EXAMPLES

General Methods

1. Fructan Determination
1.1 Fructan Determination by Hydrolysis with Exoinulinase The inulin solutions to be measured are prepared by weighing 50.0+/−5.0 mg of inulin accurately into a 1 ml graduated flask. 700 µl of dd $H_2O$ are added to dissolve. The sample is then shaken in order to detach the sample material as well as possible from the base of the vessel, and is then placed in an almost boiling waterbath (~99° C.) for 8 minutes. During the incubation, the graduated flask is shaken every 30 seconds. After the incubation, the sample is allowed to cool to room temperature and is then made up to the 1 ml mark with dd $H_2O$. The sample solution has an inulin concentration of 5.0+/−0.5%.

For sugar determination before the digestion, 200 µl are removed and frozen at −20° C. Before the sugar measurement, this sample is thawed at room temperature, mixed, dissolved by shaking at 1400 rpm in a heating block at 95° C. for 5 minutes, and centrifuged at 4000 rpm for 2 minutes. For the hydrolysis, 50 µl of the approx. 5% strength inulin solution are put into the digestion mix consisting of 50 µl of 1M Na citrate pH 4.6, 25 µl of exo-inulinase (Megazyme International Ireland Ltd, Wicklow, Ireland, article No. E-EXO1, 2.5 U/µl) and 375 µl of dd $H_2O$. The digestion is mixed and centrifuged at 4000 rpm for 1 minutes. The digestion is then incubated on a heating block at 40° C. for 4 h. All digested samples are frozen at −20° C. Before the sugar measurement, these samples are thawed at room temperature, mixed and centrifuged at 4000 rpm for 2 minutes. For the fructose measurement, a 1:10 dilution is prepared by adding 10 µl of digestion to 90 µl of dd $H_2O$.

To determine the fructose and glucose liberated in the digestion, a photometric measurement of glucose and fructose is carried out in all the samples as described under "sugar determination (glucose, fructose, sucrose)". Besides glucose and fructose, also sucrose is determined in the sample before the digestion.

The undiluted 5% strength inulin solution is used for sugar measurement before the digestion. 10 µl of this solution are added to 200 µl of measurement buffer. For glucose measurement in the digested samples, 10 µl of the undiluted samples are added to 200 µl of measurement buffer. For fructose measurement in the digested samples, 10 µl of samples diluted 1:10 are added to 200 µl of measurement buffer.

The calculation is based, as in the sugar determination, on a molar extinction coefficient of 6.23 $l*mmol^{-1}*cm^{-1}$ for the conversion of NADP to NADPH. The concentration of glucose and fructose present before the digestion is subtracted from the glucose and fructose concentrations in the digested samples. Likewise, the glucose and fructose which would be liberated from hydrolyzed sucrose present in the sample before the digestion is subtracted.

The concentrations of fructose and glucose formed during the digestion of inulin are then obtained. The fructan content is obtained by addition of the glucose and fructose contents and with inclusion of the factor 162/180 for conversion of the measured free hexoses into the hexoses bound in the fructan.

2. Sugar Determination (Glucose, Fructose and Sucrose)

The glucose, fructose and sucrose contents were determined by photometry in an enzymatic assay via conversion of $NADP^+$ (nicotinamide adenine dinucleotide phosphate) to NADPH (reduced nicotinamide adenine dinucleotide). The aromatic character of the nicotinamide ring is lost in the reduction, and thus the absorption spectrum is changed. This change in the absorption spectrum can be detected by photometry.

Glucose and fructose are converted by means of the enzyme hexokinase and adenosine triphosphate (ATP) into glucose 6-phosphate and fructose 6-phosphate. The glucose 6-phosphate is then oxidized by the enzyme glucose-6-phosphate dehydrogenase to 6-phosphogluconate. $NADP^+$ is reduced to NADPH in this reaction, and the amount of NADPH formed is measured by photometry. The ratio of NADPH formed to the glucose present in the extract is 1:1, so that the glucose content can be calculated from the NADPH content using the molar extinction coefficient of NADPH (6.23 $l\ mmol^{-1}\ cm^{-1}$) according to Lambert-Beer's law.

After the oxidation of the glucose 6-phosphate is complete, the fructose 6-phosphate which is likewise produced in the solution is converted by the enzyme phosphoglucoisomerase into glucose 6-phosphate, which in turn is oxidized to 6-phosphogluconate. The ratio of fructose and the amount of NADPH formed is also 1:1. The fructose content is calculated from the amount of NADPH formed, as described for glucose.

Subsequently, the sucrose present in the extract is cleaved by the enzyme sucrase (from Megazyme) into glucose and fructose. The liberated glucose and fructose molecules are then converted by the abovementioned enzymes in the $NADP^+$-dependent reaction into 6-phosphogluconate. Two molecules of NADPH are formed in the conversion of one molecule of sucrose into 6-phosphogluconate. The amount of NADPH formed is likewise measured by photometry, and the sucrose content is calculated therefrom using the molar extinction coefficient of NADPH.

A 5% strength inulin solution as described under "Fructan determination by hydrolysis with exo-inulinase" is used for the sugar measurement. 10 µl of this solution are added to 200 µl of measurement buffer. The measurement takes place as duplicate determination in microtiter plates using the SPECTRAmax photometers (Molecular Devices). All the enzyme solutions used are made up in measurement buffer consisting of 50 mM imidazole HCl pH 6.9, 2.5 mM $MgCl_2$ 1 mM ATP and 0.4 mM NADP. The conversion of NADP to NADPH is followed at a wavelength of 340 nm.

The glucose determination takes place by adding 2 µl of a mix of hexokinase (from yeast, 0.3 U/µl) and glucose-6-phosphate dehydrogenase (from yeast, 0.14 U/µl). After conversion of the glucose is complete, 2 µl of phosphoglucose isomerase (from yeast, 0.14 U/µl) are added to determine fructose. When the fructose is completely converted, 2 µl of sucrase (from Megazyme, 0.2 U/µl) are added to cleave the sucrose present. The calculation of glucose, fructose and sucrose takes place as described.

3. Analysis of the Molecular Weight Distribution 3.1 Gel Permeation Chromatography with Light Scattering and Refractive Index Detection (GPC-RI-Malls System)

The inulins/fructans are dissolved in extra-pure water in a concentration of 1% (w/v). Between 5 and 10 mg are weighed out into 2 ml Eppendorf vessels. The solutions are heated at 95° C. in a thermal shaker (Eppendorf) at 300 rpm for 10 minutes. After cooling to room temperature, 0.5% (w/v) solutions are prepared by 1:2 dilution with extra-pure water. Filtration takes place through 0.22 µm centrifugal filters (Spin-x, Costar) at 4000 rpm for 2 minutes. The polymers are analyzed using a Dionex System (Dionex Corporation, Sunnyvale, USA) consisting of the following components: P680 HPLC Pump, AS50 Autosampler, thermostatted column compartment TCC-100. A DAWN-EOS light scattering detector (Wyatt Technology, Santa Barbara, USA) with $\lambda_o$=690 nm and 15 detectors in the range of angles from 25.9 to 163.3° and K5 flow cell coupled to a Shodex RI-101 RI detector (Shodex Denko K.K., Kanagawa, Japan) is used for the detection. The polymers are fractionated on a precolumn and three columns (Suprema 30, Suprema Lux 1000, Suprema 30000) (SUPREMA-Gel, PSS Polymer Standards Service GmbH, Mainz, Germany). 90 of solution are injected. The fractionation takes place at a temperature of 30° C. and a flow rate of 0.8 ml/minute with 0.05M $NaNO_3$ as eluent. The Astra V 5.1.8.0 program (from Wyatt Technology, Santa Barbara, USA) is used to analyze the molecular weight distribution of the samples.

3.2 Gel Permeation Chromatography with Refractive Index Detection (GPC-RI System)

The inulins are dissolved in the eluent (DMSO+90 mM $NaNO_3$) in a concentration of 1% (w/v) by shaking gently in a thermal shaker at 95° C. for 10 minutes. After brief cooling, the inulin solution is diluted to 0.1% with eluent (100 µl of inulin solution+900 µl of eluent) and immediately placed in the autosampler at 60° C. The polymers are analyzed using the following apparatus: Dionex P580 pump, Dionex AS50 autosampler, Dionex model 585 column oven (Dionex GmbH, Idstein, Germany), Shodex RI-71 detector (Shodex/Shoko Co. LTD, Tokyo, Japan). The systems are controlled by the Chromeleon software (Dionex GmbH, Idstein, Germany). The polymers are fractionated on a PSS GRAM, 10 precolumn and the PSS GRAM 3000, 10µ and PSS GRAM 100, 10µ separation columns (PSS Polymer Standards Service GmbH, Mainz, Germany). 50 µl of the 0.1% inulin solution are injected for the analysis. The fractionation takes place in the column oven at a temperature of 60° C. and with a flow rate of 0.7 ml/minute with the eluent DMSO+90 mM $NaNO_3$. To determine the molecular masses, the system is calibrated with the following dextran standards (product No. 31430, Fluka Riedel-deHaen, Seelze, Germany): dextran T1 (Mw 1270), T5 (Mw 5220), T12 (Mw 11 600), T25 Mw 23 800), T50 (Mw 48 600), T80 (Mw 80 900), T150 (Mw 147 600), T270 (Mw 273 000), T410 (Mw 409 800) T670 (667 800). The PSS WinGPC compact V.6.20 program (PSS, Mainz, Germany) is used to analyze the molecular weight distribution of the samples.

4. Determination of the Water Content

The water content is determined using an AQUA 40.00 Karl-Fischer titrator (from analytikjena AG). Hydranal-Coulomat AG (Riedel-deHaën, article No. 34 836) is used as anolyte. The reference substance used is dibasic sodium tartrate dihydrate (Riedel-deHaën, article No. 32 323) with a moisture content of 15.61-15.71%. 10-20 mg of sample are weighed into 5 ml sample bottles (N20-5DIN, Machery-Nagel, article No. 702 04.36), the bottles are closed with crimped caps (N20 TS/oA, Machery-Nagel, article No. 702 815), and the water content of the sample is determined using the Karl-Fischer titrator.

5. Determination of the Degree of Branching

The inulins are initially permethylated and the completeness of the methylation is checked by ATR-IR spectroscopy (see below for apparatus and conditions). The samples were then decomposed by acidic hydrolysis (standard methylation analysis) or alternatively by reductive degradation into their monomer building blocks, and the relative molar composition was determined by gas chromatography (see below for apparatus and conditions) and gas chromatography mass spectroscopy (GC-MS, see below for apparatus and conditions) of the partially methylated alditol acetates and anhydroalditol acetates.

| ATR-IR | |
|---|---|
| Apparatus: | Bruker Tensor 27 |
| Technique: | Diamond ATR |
| GC: | |
| Apparatus: | Carlo Erba HRGC 5160 Mega Series |
| Column: | Chrompack CPSil8CB (25 m) with retention gap (1.5 m) ID: 0.25 mm  FD: 0.25 µm |
| Carrier gas: | He (80 kPa) |
| Detector: | FID |
| Injector: | on column |

| ATR-IR | |
|---|---|
| Integrator: | Merck Hitachi D-2500 Chromato-Integrator |
| Temperature program: | 60° C. (1 min isothermal), 10° C./min to 170° C., 3° C./min to 230° C., 20° C./min to 290° C. (20 min isothermal) |

| GC-MS | | |
|---|---|---|
| GC: | Apparatus: | Agilent 6890 GC |
| | Column: | HP-5, 30 m |
| | Carrier gas: | He |
| | Injector: | Split 5:1 |
| | Temp. program: | 60° C. (1 min isothermal), 10° C./min to 170° C., 3° C./min to 230° C., 20° C./min to 290° C. (20 min isothermal) |
| MS: | Apparatus: | JEOL GCmate II double-focussing sector field spectrometer |
| | Mode: | EI, 70 eV |
| | Evaluation: | AMDIS32, Wsearch32 |

5.1 Permethylation (according to Ciucanu and Kerek/Ciucanu, Kerek, F. (1984) A simple and rapid method for the permethylation of carbohydrates. Carbohydr. Res. 131, 209-217.)

About 50 mg of sample are dissolved in 2.5 ml of dimethyl sulfoxide. Then 3 eq/OH of finely ground sodium hydroxide and 3 eq/OH of methyl iodide are added and stirred at room temperature for 24 hours. Then half the amount of each of the reagents is added once again. The samples are subsequently dialyzed against distilled water for four days (Dialysemembran Spectra/Por MWCO 3500, Spectrum Laboratories, Rancho Dominguez, Calif., USA) and freeze dried. The completeness of the methylation is checked by ATR-IR spectroscopy. The OH stretching vibration in the range 3300-3400 $cm^{-1}$ should have disappeared if there is permethylation.

5.2 Standard Methylation Analysis

Hydrolysis

About 2 mg of permethylated inulin are mixed in a 1 ml V vial with 0.9 ml of 0.5 M trifluoroacetic acid and hydrolyzed by stirring at 90° C. for one hour. After the solution has cooled it is evaporated to dryness in a stream of nitrogen. Trifluoroacetic acid residues are removed by codistillation with toluene.

Reduction

The hydrolyzed sample is mixed with 500 of a 0.5 M $NaBD_4$ solution in 2 M $NH_3$ and heated at 60° C. for one hour. After cooling, excess sodium borohydride is decomposed by adding a few drops of glacial acetic acid. Resulting borate is removed by codistillation with 15% strength methanolic acetic acid.

Acetylation

The partially methylated sugar alcohols resulting from the reduction are mixed with 200 μl of acetic anhydride and 50 μl of pyridine and acetylated at 90° C. for 2 hours. The solution is cooled and then saturated sodium bicarbonate solution is added until no further gas formation is to be observed. It is then extracted four times with 15 ml of dichloromethane each time. The combined organic phases are washed twice with 15 ml of saturated $NaHCO_3$ solution each time, once with 20 ml of cold 0.1 M HCl and once with 25 ml of distilled water. The solution is then dried over calcium chloride and concentrated in vacuo, and taken up in dichloromethane for the GC measurement.

5.3 Reductive Degradation

About 1 mg of the permethylated sample is dissolved in 500 μl of dichloromethane in a screw-cap glass vial, mixed with 6 eq/glycoside bond on triethylsilane and 4 eq of TMS triflate and stirred at room temperature for 2 hours. After addition of 20 μl of acetic anhydride, stirring is continued at room temperature for 2 hours. The reaction is then stopped by adding saturated aqueous $NaHCO_3$ solution, and stirring is continued for 1 hour. Working up takes place by extraction with dichloromethane and subsequent washing of the combined organic phases with saturated aqueous $NaHCO_3$ solution and distilled water. The solution is finally dried over calcium chloride, concentrated in a stream of nitrogen and taken up in dichloromethane for the GC measurement.

5.4 Qualitative and Quantitative Analysis

The degradation products were analyzed quantitatively by gas chromatography with on-column injection and flame ionization detector (FID). The peak areas were corrected according to their effective carbon response. The peaks were assigned on the basis of their mass spectrum (GC-MS) and the retention times of known comparison samples.

6. Differential Scanning Calorimetry of Inulin 40 ml of a 15% strength (w/v) inulin solution were prepared in 50 ml graduated polypropylene tubes (30.0×115 mm, from Greiner, order number 227261). This was done by adding the respective powder to double-distilled water and shaking. Subsequently, all the prepared suspensions are placed in a waterbath (95° C.) and dissolved by shaking several times. After 20 minutes, it is established visually that all the suspensions have completely dissolved. The prepared solutions are then divided in equal parts to two 50 ml graduated polypropylene tubes (30.0×115 mm, from Greiner, order number 227261) and immediately deep frozen in liquid nitrogen. The frozen solutions were then freeze dried for two days (water content about 10%) and ground in a mortar.

The water content of the samples is determined using an automatic Karl-Fischer titrator (see general methods 4).

For a DSC measurement, about 10 mg of inulin dry substance are weighed into a stainless steel crucible (volume 50 μl), the exact weight is found, and 30 μl of distilled water are added. The crucibles are then hermetically sealed. An empty stainless steel crucible is used as reference. The sample is heated in a DSC apparatus with autosampler (Perkin Elmer; Diamond) from 10-160° C. at a heating rate of 10° C./minutes. The data analysis is carried out by the PYRIS 7.0 software program (Perkin Elmer, 63110 Rodgau-Jügesheim, Germany). This entailed determination of $T_O$ (onset) and the free enthalpy dH.

7. Viscosity Determination

Aqueous inulin solutions of various concentrations (weight per volume of distilled water) were prepared by shaking at 98° C., and the clear solutions were measured immediately after a dissolving time not exceeding 13 min. The measurements were carried out in a BOHLIN Gemini Advanced Rheometer (Malvern Instruments; Herrenberg, Germany) using the isothermal (90° C.) viscosimetry mode on a CP4°/40 mm cone-plate system. The measuring gap was covered with a layer of extra light paraffin oil. A shear rate of 10 $s^{-1}$ for 60 s with a 10 s relaxation time was used for preshearing. The shearing was measured in logarithmic steps in a shear rate mode. The initial shear rate was 20 $s^1$, the final shear rate was 30 $s^{-1}$ in an increasing ramp with a holdup time of 20 s an integration time of 10 s. The data are based on the average values in the range from 20 $s^{-1}$ to 30 $s^{-1}$ and are the means of three independent measurements per data point. All measurements specified as outliers are not included in the average values. The definition of "outlier" took place by the so-called "quartile method". This entailed outliers being specified as all measurements lying outside the range criterion $Q_2-k*(Q_3-Q_1) \leqq$ no outlier $\leqq Q_2-k*(Q_3-Q_1)$ (SACHS, Lothar: Angewandte Statistik, 10th edition, Springer-Verlag Berlin (2002), pp. 364 et seq.). $Q_1$ and $Q_3$ here is the 25% quartile and the 75% quartile, respectively, and $Q_2$ is the median (50% quartile) of the measured data. A value of 1.5 was used for the factor k.

8. Determination of Gel Strength and Viscoelastic Behavior 70 g of a 17% by weight suspension of inulin in water (distilled) was put into an MV measuring cup of a Haake Rotovisco VT 550 viscometer. A paddle stirrer was then inserted and mounted in the preheated (90° C., heating jacket) apparatus. The mixture was then heated with stirring at 128 rpm for 15 min.

After 15 min, the mixture was transferred at 90° C. into a container which consisted of a base and a wall composed of two cylindrical rings of acrylic sheet (each 20 mm high, 30 mm diameter) which were placed one on top of the other and were fastened together by means of an adhesive tape (19 mm wide). The mixture was introduced into the container without bubbles until the level was about 5 mm below the upper edge. The container was then hermetically covered with an aluminum foil and left to stand at room temperature (23° C.) overnight.

The gel strength was measured after storage at room temperature (23° C.) for about 20 hours using a TA XT2 texture analyzer. To make measurement of the gel strength possible on a smooth, undried surface, firstly the adhesive tape which held the two cylindrical rings of the container together was removed. The gel was then divided with a razorblade between the rings so that the lower part of the gel exhibited a smooth surface.

The gel strength was measured with the TA XT2 texture analyzer by a level dome (diameter 24.5 mm) penetrating (1 mm) into the gel. The settings on the texture analyzer were as follows:

| Measurement principle: | force in direction of pressure |
|---|---|
| Forward speed: | 2 mm/s |
| Test speed: | 2 mm/s |
| Trigger value: | 0.01 N |
| Reverse speed: | 2 mm/s |
| Travel: | 1 mm |

The maximum value with a single penetration of the dome in newtons is indicated.

Example 1

Characterization of the Inulin from Artichoke Roots

1. Cultivation of the Artichoke Plants

The artichoke plants of the Madrigal variety were grown in the vicinity of Valencia, Spain. The seeds were sown in April 2005, and the plants were harvested in August/September 2005. The roots were separated from the above-ground part, freed of adherent soil and dried. The roots were then transported without cooling from Spain to Germany. The roots were stored at −20° C. until the inulin was extracted.

2. Inulin Preparation from Artichoke Roots

Roots from artichoke plants of the Madrigal variety about 4-5 months old are used to prepare the inulin. 60 kg of roots are freed of the soil constituents adhering to them by washing in the deep-frozen stage with a high-pressure cleaner (Kärcher 240) before they are further processed to chips in a shredder (Gloria Universal garden shredder natura 2800L). The chips are put into a jacket-heated extracter with gate agitator containing water preheated to 80-90° C. The total amount of water added is 180 kg. The pH of the extract is adjusted to 9.0 by adding NaOH. After rapid heating of the chip mash from 40° C. to 80-85° C. via the jacket of the extractor, the mash is agitated at 80-85° C. for about 60 minutes in order to extract the inulin (fructan) from the chips. After this time, crude extract is separated from the chips by pumping off.

The crude extract is decolorized in a two-stage process by forming a total of 0.7 g of $Mg(OH_2)$/100 ml of extract. In the first stage, 3400 g of $MgSO_4*7\ H_2O$ (equivalent to 0.5 g of $Mg(OH_2)$/100 ml of extract) are dissolved in 170 L of dark-brown colored extract with stirring over the course of 10 minutes. Subsequently, 1015 g of 96% strength $Ca(OH)_2$ are added as suspension in 3 L of water and stirred for 10 minutes. A pH of 9.4 is set up. The whole precipitation mixture is quantitatively clarified in a plate separator (GEA Westfalia type SC-6-06-076) over the course of 120 minutes. The decolorized extraction solution has a pale yellow color and is free of materials causing turbidity. A solid phase in the form of a thick paste is obtained as removed sludge fraction. The entire decolorization step is repeated on the extraction solution obtained in this way and comprising 150 L with $MgSO_4*7\ H_2O$ (equivalent to 0.2 g $Mg(OH_2)$/100 ml of extract) and 410 g of 96% strength Ca(OH), as suspension in 1.5 L of water. The whole precipitation mixture is quantitatively clarified in a plate separator over the course of 30 minutes. The decolorized extraction solution with a pH of 9.4 is clear, has a pale yellow color and is free of materials causing turbidity. A centrifugate in the form of a thick paste is again obtained as sludge fraction.

Solid inulin is obtained from the extract brightened in this way by cooling at a temperature of 4° C. over a period of 48 h. The inulin is obtained as sludge-like sediment by centrifugal deposition using the plate separator.

The sediment is further purified twice in succession in the same concentration as present in the brightened extract by dissolving the inulin in hot water and renewed precipitation by storage at 2° C. for 48 h. The inulin sediment finally obtained is again completely dissolved in the same concentration as previously used in water with input of heat. The hot solution is then filtered through a plate filter with filter layers. The inulin is subsequently precipitated by cooling the solution (2° C., 48 h) and the final product is freeze dried.

FIG. 1 shows a diagrammatic representation of the progress of the extraction.

Figure 2:
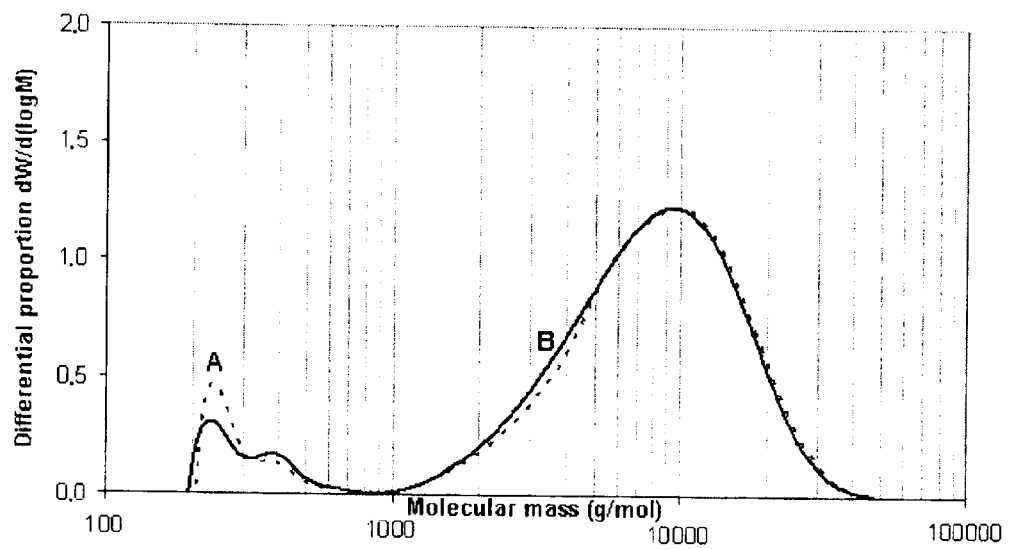
FIG. 2 shows a GPC-RI analysis of the polymer distribution in washed artichoke roots (A) and the extract after the hot-water extraction inulin (B).

During the extraction process, the polymer distribution was analyzed after the individual extraction and purification steps by gel permeation chromatography with refactor index detection and calibration with dextran standards (GPC-RI, see Method 3.2 in "General Methods"). As evident from FIG. 2, the polymer distribution of extract (B) after the hot-water extraction is comparable to that in the washed roots (A). FIG. 2 shows a GPC-RI analysis of the polymer distribution in the washed artichoke roots (A) and the extract after the hot-water extraction of inulin (B).

Figure 3:
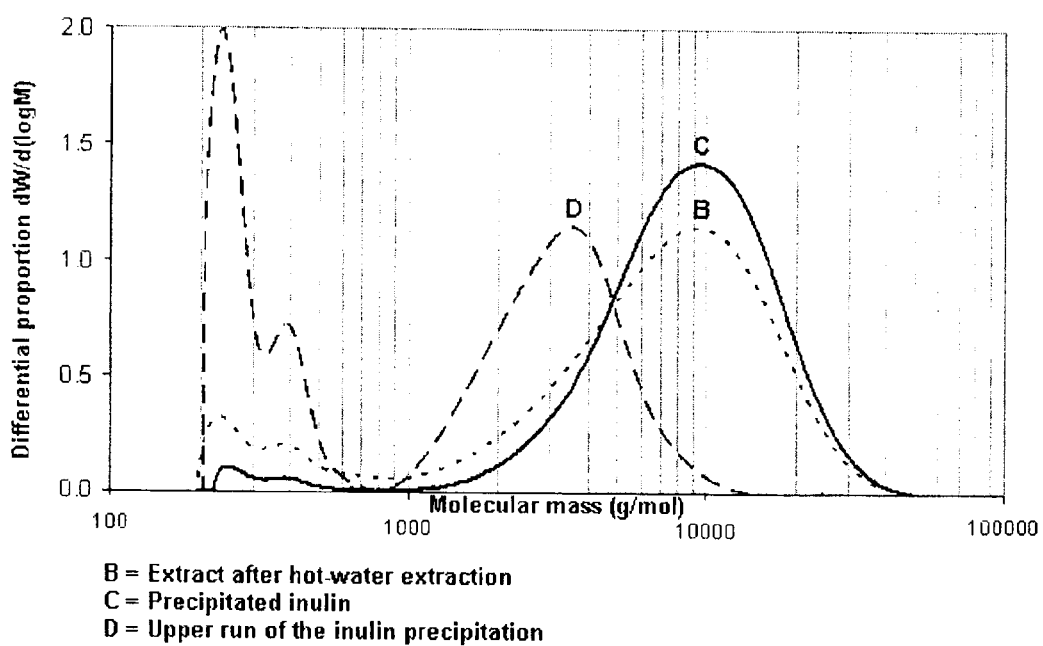
FIG. 3 shows a GPC-RI analysis of the polymer distribution in the extract after the hot-water extraction of the inulin (B), in the sediment after the inulin precipitation at 4° C. (C) and in the upper run obtained after centrifugation of the inulin after precipitation (D).

Analysis of the polymer distribution after the cold (4° C.) fractionation of the inulin showed that a high molecular weight inulin fraction (C) was separated from a low molecular weight fraction (D) (FIG. 3). FIG. 3 shows a GPC-RI analysis of the polymer distribution in the extract after the hot-water extraction of inulin (B), in the sediment after the inulin precipitation at 4° C. (C) and in the upper run obtained after centrifugation of the inulin after precipitation (D).

Figure 4:
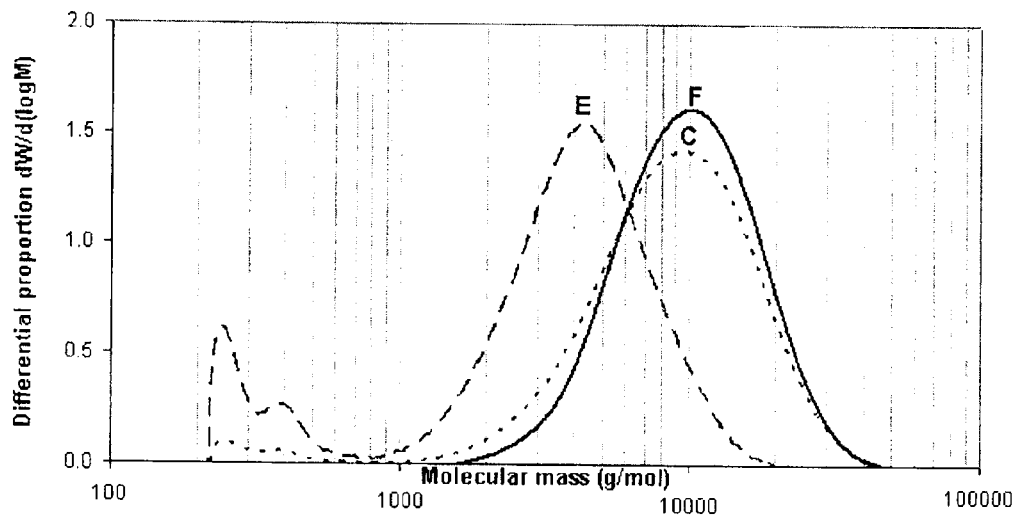
FIG. 4: GPC-RI analysis for the polymer distribution in the inulin precipitated at 4° C. (C), in the sediment after the reprecipitation (F) and in clear phase after the reprecipitation (E).

A further enrichment of high molecular weight inulin and a depletion of low molecular weight substances, especially mono- and disaccharides, was achieved by reprecipitation of the high molecular weight inulin fraction (FIG. 4). FIG. 4 shows a GPC-RI analysis of the polymer distribution in the inulin precipitated at 4° C. (C), in the sediment after the first reprecipitation (F) and in clear phase I after the first reprecipitation (E).

Figure 5:
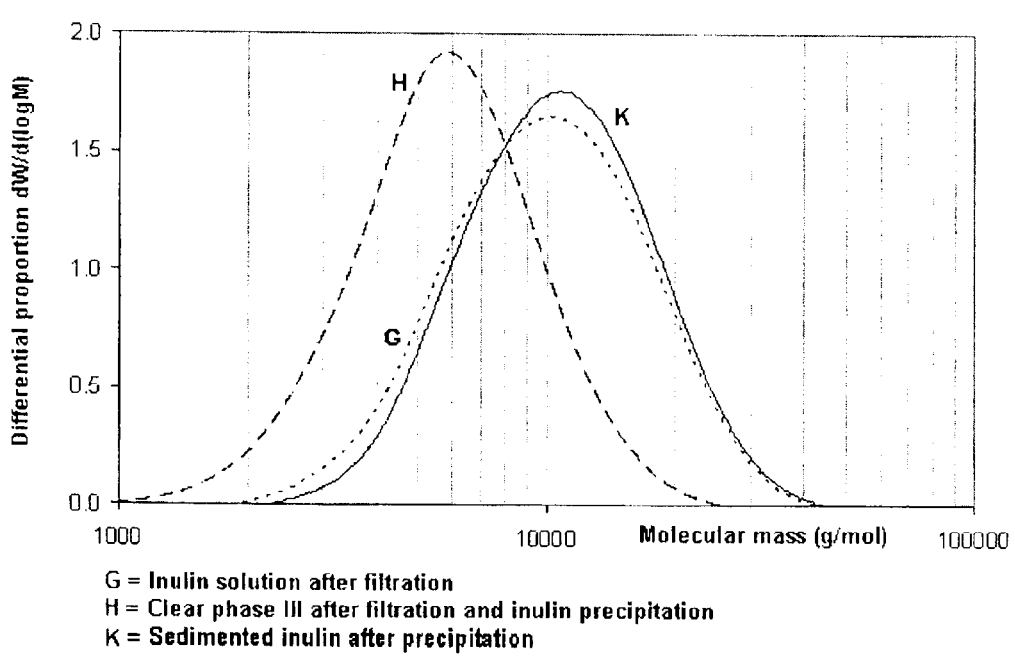
FIG. 5: GPC-RI analysis of the polymer distribution in inulin solution after filtration (G), the sedimented inulin after the crystallization (K) and clear phase III after the crystallization (H).

Inulin with a lower degree of polymerization remained in the clear phase likewise after the renewed precipitation of inulin after the hot-water filtration (FIG. 5). FIG. 5 shows a GPC-RI analysis of the polymer distribution in inulin solution after filtration (G), the sedimented inulin after the crystallization (K) and clear phase III after the crystallization (H).

3. Determination of the Purity of the Prepared Inulin

The purity of the artichoke inulin obtained in section 2 was determined by determining the fructan and water contents of the freeze-dried material. The water content determined for the artichoke inulin was 2.9% (see method "Determination of the water content").

The fructan content was determined by hydrolyzing the inulin with the enzyme exo-inulinase (see method "Fructan determination by hydrolysis with exoinulinase"). The purity based on dry matter (DM) was found from the fructan content and the water content. Purity=fructan content×100/(100−water content)

As is evident from Table 1, the average degree of purity of the prepared artichoke inulin is 96% of the dry matter (DM).

TABLE 1

Determination of the purity of the prepared artichoke inulin

| | | Exo-inulinase digestion | |
|---|---|---|---|
| Material | Water content [%] | Fructan [% of initial weight] | Purity [% TM] |
| Artichoke inulin | 2.9 | 93% ± 7% | 96% |

4. Molecular Weight Determination by GPC-RI-MALLS 0.5% (w/v) aqueous solutions were prepared from the purified artichoke inulin obtained in section 2, and from purchased reference samples of Raftiline HP (from Orafti, batch: HPBNH4DNH4) and inulin from dahlia tubers (from Sigma, article number I-3754, batch: 75H7065), and the molecular mass distribution of the inulins vas determined by gel permeation chromatography (see method 3.1). This distribution is depicted in FIG. 5, and the molecular masses (anhydrofructose=162 g/mol) and average chain lengths calculated therefrom have been summarized in Table 2.

Analysis of the molecular weight distribution using the GPC-RI-MALLS system resulted in a weight average molecular mass Mw of 13 995 g/mol and a number average molecular mass Mn of 11 620 g/mol for the artichoke inulin. This corresponds to an average chain length of 86 for DPw and of 72 for DPn. The chain lengths of the purified artichoke inulin are on average distinctly longer than those of Raftiline HP (DPw=36, DPn=29) and of dahlia inulin (DPw=41, DPn=33). This is also reflected in the minimum and maximum molecular masses, which are distinctly larger for artichoke inulin.

TABLE 2

Molecular mass distribution of various inulins

| Material | $M_w$ [g/mol] | $M_n$ [g/mol] | Polymer distribution (min-max) [g/mol] | DPw | DPn | Molecular dispersity |
|---|---|---|---|---|---|---|
| Artichoke inulin | 13 995 | 11 620 | 1377-33 099 | 86 | 72 | 1.19 |
| Raftiline HP | 5823 | 4759 | 999-15 162 | 36 | 29 | 1.24 |
| Dahlia inulin | 6678 | 5358 | 1139-19 569 | 41 | 33 | 1.24 |

5. Results of Glucose, Fructose and Sucrose Determination

The proportion of glucose, fructose and sucrose in the artichoke inulin obtained in section 2 was determined by photometric determination of the sugars in 5% strength inulin solutions as described in Method 3 ("Sugar determination").

As is evident from Table 4, the glucose, fructose and sucrose contents in the purified artichoke inulin are less than 0.1% of the inulin powder.

TABLE 3

Content of glucose, fructose and sucrose in purified artichoke inulin

| Material | Glucose (g/100 g inulin powder) | Fructose (g/100 g inulin powder) | Sucrose (g/100 g inulin powder) |
|---|---|---|---|
| Artichoke inulin | <0.1% | <0.1% | <0.1% |

6. Degree of Branching 6.1 Standard Methylation Analysis

The degree of branching was measured in an inulin sample of the invention having a DPw of 90 and a DPn of 84.

The comparative examples used were Raftiline HP (from Orafti, batches HPBNO3DNO3 and HPBNH4DNH4) and inulins from dahlia tubers (from Sigma, article number I-3754, batch: 022K7045 or 75H7065) and Jerusalem artichoke roots (Sigma, article number I-2880 batches 111H7045 and 88F7220) the degree of branching were determined by means of methylation analysis (see General Methods, 5.1).

Hydrolysis, reduction and acetylation of 2-1-linked fructans result in 1,2,5-tri-O-acetyl-3,4,6-tri-O-methyl-D-mannitol and -sorbitol. The terminal fructosyl radicals afford 2,5-di-O-acetyl-1,3,4,6-tetra-O-methyl-D-mannitol and -sorbitol. A terminal glucopyranosyl unit results in 1,5-di-O-acetyl-2,3,4,6-tetra-O-methyl-D-sorbitol. Building blocks additionally branched in position 6 give the corresponding 1,2,5,6-tetra-O-acetyl-3,4-di-O-methylalditols.

Besides the products indicating 2-1 linkage, it was possible to detect in all fructan samples those from terminal fructose and glucose building blocks. The chromatograms additionally showed difructose dianhydride (DMA, approx. 3 mol %) which is formed on removal of TFA in a stream of nitrogen from 2-1 linked fructose.

From the mass spectra it was additionally possible to identify products resulting from a 2-1,6 linkage in all the samples. 1,3- and 1,4-acetylated compounds were also identified, which would arise with branches in positions 3 and 4, respectively, but may also derive from incomplete methylation. The nonspecific occurrence of 1,3- and 1,4-acetylated products is an indicator of submethylation. Assuming that position 6 is affected by submethylation to the same extent as positions 3 and 4, the nonspecific proportion (average of 1,3-Ac and 1,4-Ac compounds) is subtracted from the proportion of 2-1,6-branched fructose units. Table 4 below shows the results resulting therefrom.

TABLE 4

| Sample | | 2-1,6-Fructose [mol %]* |
|---|---|---|
| Inulin | Artichoke | 1.4 |
| | Raftiline HP | 0.4 |
| | Dahlia | 0.2 |
| | Jerusalem artichoke | not detected |

*based on all species found

Evaluation of the methylation analysis revealed a degree of branching of 1.4 mol % for the artichoke inulin. The degree of branching of this inulin is thus distinctly higher than that in the inulins of the reference samples from chicory (RaftilineHP), dahlia and Jerusalem artichoke.

6.2 Reductive Degradation

Consistent with the standard methylation analysis, it is possible to identify by reductive glycoside cleavage the corresponding products of terminal glucopyranose (1,5-anhydro-2,3,4,6-tetra-O-methyl-D-sorbitol), of terminal fructofuranose (2,5-anhydro-1,3,4,6-tetra-O-methyl-D-mannitol and -sorbitol) and 2-1 linked fructofuranose (1-O-acetyl-2,5-anhydro-3,4,6-tri-O-methyl-D-mannitol and -sorbitol) in all the samples. It is also possible for all the fructans to detect from the mass spectra the products resulting when a 2-1,6 linkage is present (1,6-di-O-acetyl-2,5-anhydro-3,4-di-O-methyl-D-mannitol and -sorbitol). In addition, 2,6-di-O-acetyl-1,5-anhydro-3,4-di-O-methylmannitol occurs, which is a rearrangement product resulting from 2-1,6-linked fructose units.

Once again, products of nonspecific submethylation (see 6.1) were detected in the GC-MS. A small proportion of unseparated open-chain alditols also appeared. These small proportions were taken into account in the 2-1 linkage. Subtraction of the nonspecific proportions results in a degree of branching (=proportion of 2-1,6-linked fructose) of 1.7 mol % for the inulin of the invention.

Example 2

Properties of the Inulin from Artichoke Roots

All the following investigations relate to the artichoke inulin of the invention detailed previously in Tables 2. The comparative Raftiline HP and dahlia inulins are likewise those detailed in Example 1.

1. Differential Scanning Calorimetry Investigation of Inulin

The differential scanning calorimetric analysis of inulin (for procedure: see methods) showed distinct differences between the various materials (see Table 5) in relation to the melting behavior. Both inulin samples differed greatly in relation to the enthalpy of fusion. This was above 25.2 J/g for artichoke inulin and only 22.8 J/g for Raftiline HP. The differences in $T_{onset}$ (To) were likewise pronounced. The initial melting temperature for artichoke inulin was 41.1° C. which was more than 3° C. higher than for the comparative chicory inulin. This increased thermal stability of artichoke inulin may be a considerable advantage in certain thermal processes in the food products sector, because the artichoke inulin is distinctly less sensitive to high temperatures than chicory inulin.

TABLE 5

| Material | To [° C.] | Enthalpy of fusion dH [J/g] |
|---|---|---|
| Artichoke inulin | 41.1 | 25.2 |
| Raftiline HP | 37.8 | 22.8 |

2. Viscosity

TABLE 6

Comparison of the dynamic viscosity of chicory inulin and artichoke inulin in water as a function of the concentration (T = 90° C.)

| Concentration | Viscosity (mPas) | |
|---|---|---|
| % (w/v) | Raftiline HP (chicory) | Artichoke inulin |
| 10 | 2.4 | 2.3 |
| 24 | 4.3 | 6.8 |
| 26 | 4.2 | 7.5 |
| 28 | 4.5 | 26.3 |

As is evident from the above table, both inulins showed at concentrations of up to 24% (w/v) very low viscosities at 90° C. (water=1 Pas). The inulin of the invention became viscous at concentrations of 26% (w/v) and especially at 28%, whereas Raftiline HP remained very similar in its viscosity to water up to 28% (w/v).

3. Particle Size after Freeze Drying

The freeze-dried sample from example 1 DPw=86, was ground in a knife mill. (Grindomix GM200, Retsch Technologie GmbH, Haan, Germany) and the particle size was determined by sieve analysis (vibrating sieve machine "Analysette 3" from Fritsch, frequency 2.0, sieving aids: 8 agate balls (10 mm Ø)/sieve, sieving time 1-2 min, amount loaded about 50 g). The result is shown in table 7 below. It was possible to determine the average particle diameter by sieve analysis as 108 μm. An inulin prepared in analogy to example 1 and having a DPw of 93-94 was also freeze dried, ground in a knife mill and investigated by sieve analysis (table 8). An average particle size of 160 μm resulted.

TABLE 7

Sieve analysis of inulin DPw = 86:

| Mesh width/μm | Mass/g | % |
|---|---|---|
| <63 | 14.00 | 28.97 |
| <90 | 6.35 | 13.14 |
| <125 | 7.54 | 15.60 |
| <160 | 5.53 | 11.44 |
| <200 | 4.75 | 9.83 |
| <500 | 10.05 | 20.79 |
| >500 | 0.11 | 0.23 |
| Total | 48.33 | 100.00 |

TABLE 8

Sieve analysis of inulin DPw = 94:

| Mesh width/μm | Mass/g | % |
|---|---|---|
| <63 | 8.33 | 16.74 |
| <90 | 3.92 | 7.88 |
| <125 | 6.17 | 12.40 |
| <160 | 6.05 | 12.16 |
| <200 | 7.60 | 15.28 |

TABLE 8-continued

| Sieve analysis of inulin DPw = 94: | | |
|---|---|---|
| Mesh width/μm | Mass/g | % |
| <500 | 17.62 | 35.42 |
| >500 | 0.06 | 0.12 |
| Total | 49.75 | 100.00 |

4. Spray Drying

The inulin (DPw=86, table 2) prepared in example 1, No. 2, was, after an intermediate freeze drying, redissolved and then spray dried on a Glatt GPCG3.1 fluidized bed spray-drying unit. For this purpose, freeze-dried inulin was introduced into water, heated to 85-90° C. and dissolved. The heated solution was spray dried with varying outlet air temperature, and the process properties and product properties were observed. The inlet temperature was kept constant at 120° C.

TABLE 9

| | Spray drying parameters | | | |
|---|---|---|---|---|
| Test/ | Composition of feed | | Temp. of feed/ | Temp. of outlet | Residual moisture |
| Sample | water/% | inulin/% | ° C. | air/° C. | KFT/% |
| Test 1 | 80 | 20 | 85-90 | 85 | 3.1 |
| Test 2 | 80 | 20 | 85-90 | 80 | 2.1 |
| Test 3 | 80 | 20 | 85-90 | 70 | 5.1 |
| Test 4 | 70 | 30 | 85-90 | 60 | 6.1 |

A spray granulation (test 5) was also carried out in addition to the spray drying. The relevant process parameters are detailed in the table below. Initially introduced as granulation seeds were 70 g of spray-dried material which was prepared as follows: Büchi B-191 spray dryer, feed: 20 g of water and 4 g of inulin (DPw=86), T (feed)=80-90° C., T (inlet)=120° C., T (outlet air)=93-94° C., aspirator rate 80%, pump rate 10%, air flow nozzle 450 l/h. The resulting granules were of very good quality in form and consistency. The granulation was possible up to an outlet air temperature of 52° C.

TABLE 10

| | Spray granulation | | | |
|---|---|---|---|---|
| Test/ | Composition of feed | | Temp. of feed/ | Temp. of outlet | Residual moisture |
| Sample | water/% | inulin/% | ° C. | air/° C. | KFT/% |
| Test 5 | 70 | 30 | 90 | variable | 5.3 |

A sieve analysis as described above revealed the following average particle diameters:

| Test 2 | 85 μm |
|---|---|
| Test 5 | 300 μm |

5. Crystallinity

Inulin samples in powder form were prepared without further pretreatment in a 2 mm-thick sample carrier (standard) between two PET covering films. A 1 mm sample carrier was used for sample 2 (see below). The X-ray measurements were carried out with a D5000 two-circle diffractometer from Bruker-AXS in symmetrical transmission using monochromatic (Ge(111) monochromator) Cu—Kα radiation. The recordings were made at 30 mA and 40 kV in the 2θ angle range of 3-29° (step width Δ2θ=0.1°) and 29.5-104 (step width Δ2θ=0.5), step/Δ2θ: 60 seconds.

Software based on the Ruland-Vonk method (WAXS 7, developed by the Fraunhofer Institut für angewandte Polymerforschung, Potsdam (Germany), described in http://edocs.tu-berlin.de/diss/2003/rihm_rainer.pdf, pp. 19 et seg.) was used to find the degree of crystallinity $x_c$, the crystallite sizes $D_{(hkl)}$ and the disorder parameter k, which is a measure of the disturbance of the lattice in the crystallites, from the scattering plots. The scattering plot for sample 2 (see below) was used as amorphous background file. Fructose was used as chemical basis, calculated with a density of 1.65 g/cm$^3$. The crystallite sizes $D_{(hkl)}$ were determined from the half-widths of the X-ray reflections by the Scherrer formula at the first two main interferences at 2θ=8° and 12°.

The samples from the spray-drying tests 1-5 detailed above, and the following samples, were measured:

Test 6: Inulin with DPw=86, prepared as described in example 1, No. 2, and freeze dried.

Test 7: Sample 1 dissolved in water at 80-90° C. and spray dried under the following conditions: Büchi 190 spray dryer, T (feed)=80-90° C., T (inlet)=120° C., T (outlet air)=80° C., air flow 450 l/h, inulin concentration=20% by weight.

Test 8: Sample 1 suspended in water at 25° C. and spray dried under the following conditions: Büchi 190 spray dryer, T (feed)=80-90° C., T (inlet)=120° C., T (outlet air)=80° C., air flow 450 l/h, inulin concentration=20% by weight.

The measured degrees of crystallinity and disorder parameters are indicated in table 11 below.

TABLE 11

| | Crystallinity $x_c$ [%] | Disorder parameter k [$10^{-2}$ nm$^2$] | $D_{(hkl)}$ 2θ = 8° [nm] | $D_{(hkl)}$ 2θ = 12° [nm] |
|---|---|---|---|---|
| Test 1 | amorphous | — | — | — |
| Test 2 | amorphous | — | — | — |
| Test 3 | 5-10 | — | — | — |
| Test 4 | 38 | 2.9 | 7.0 | 9.6 |
| Test 5 | 45 | 2.9 | 6.9 | 9.4 |
| Test 6 | 33 | 4.4 | 5.5 | 7.1 |
| Test 7 | amorphous | — | — | — |
| Test 8 | 15 | 3.2 | 8.1 | 9.9 |

6. Structure Formation of the Inulins after Heating in Water 15 ml portions of 20% strength suspensions of the inulins in water were each made up in aluminum beakers (RVA-3d beakers from Winopal Forschungsbedarf GmbH; volume about 70 ml, diameter 38 mm), stirred up and equipped with a magnetic stirring bar and finally covered. The suspensions were heated using a multithermal stirrer (VARIOMAG Multitherm 15 from H+P Labortechnik AG) with stirring. The temperature was controlled in this case by using a PT 100 probe (accessory for the VARIOMAG Multitherm 15) which stood in a covered reference beaker with distilled water on the heating block. The multithermal stirrer was preheated so that the temperature of the reference sample remained stable at 90° C. The suspensions to be heated were placed on the multithermal stirrer and stirred at 90° C. for 8 min. The samples were then removed from the multithermal stirrer stored at room temperature for 24 hours. The strength of the resulting gels was then measured using a TA-TX2 texture analyzer (Stable Micro Systems). This measurement was carried out using the SMSP/0.5 8076 penetrating plunger (Stable Micro Systems) with a diameter of 12 mm as measurement system. The following parameters were applied for the TA measurement with the 5 kg measuring cell:

Options: measure force in direction of pressure
Single test
Parameter: forward speed 2.00 mm/s
Test speed 0.50 mm/s
Reverse speed 0.50 mm/s
Travel (depth of penetration) 3 mm
Trigger force 2 g The structure-forming behavior of various inulins after thermal treatment in water was investigated. It emerged from this that the inulins from chicory (Raftiline HP® and Beneo HPX®) do not form gel-like structures under these conditions (table 12). In contrast thereto, the inulins of the invention (DPw=86 or 94 from freeze drying) form very strong structures. Surprisingly, the sample in which the spray-dried inulin with DPw=86 was used also formed considerably stronger gels than the comparable samples in which the inulin was freeze dried. This is particularly clear from the fact that the gel strengths found with only 15% (w/w) concentration of inulin employed were still distinctly higher than those with the freeze-dried comparative samples at 20%.

TABLE 12

Structure formation of the inulins after heating in water

| | Inulin concentration, % (w/w) | Gel strength [g] | Standard deviation |
|---|---|---|---|
| Raftiline HP ® DPw = 36 | 20 | No gel | — |
| Beneo HPX ® DPw = 33 | 20 | No gel | — |
| Inulin DPw = 86 | 20 | 353 | 92** |
| Inulin DPw = 94 | 20 | 493 | 31* |
| Inulin DPw = 86, spray dried | 20 | 1182 | 347** |
| Inulin DPw = 86, spray dried | 15 | 539 | 93* |

*n = 2
**n = 4

7. Prebiotic Properties

The prebiotic effect of inulin according to the invention was investigated in an in vivo model study in a three-stage fermentation system (bowel model). The types of bacteria which colonize the fermentation system, and their metabolic activities (formation of short-chain fatty acids), were ascertained.

1. Materials and Methods:
a) Continuous Three-Stage Culture System:

A continuous three-stage culture system which has previously been described by Pereira et al. (2003) Appl Environ Microbiol 69(8), 4743-4752 and Probert et al. (2004) Appl Environ Microbiol 70, 4505-4511, was used in this study. The bowel model consisted of three culture vessels V1, V2 and V3 with working volumes of 0.28, 0.30 and 0.30 liters which were arranged in series. Each vessel was provided with a magnetic stirrer, the temperature was kept at 37° C. by means of a waterbath, and the pH in the individual vessels was controlled by an Electrolab pH controller. The entire system (including media reservoir) was operated under anaerobic conditions by passing sterile oxygen-free nitrogen through the liquid. The pH in the three vessels was adjusted by adding the appropriate amount of 0.5 M HCl—NaOH to 5.5 (V1), 6.2 (V2) and 6.8 (V3). Vessel 1 simulated the microbial conditions in the anterior large bowel. It was relatively rich in nutrients, had a relatively more acidic pH and a shorter residence time than vessel 3 with a more neutral pH and comparatively little substrate. Vessel 3 simulated the posterior part of the large bowel. Vessel 2 modeled the central, transverse part of the large bowel (transverse colon).

Oxygen-free nitrogen was continuously blown into the sterile culture medium, and it was introduced by means of a peristaltic pump into V1 which led sequentially to V2 and V3. The culture medium consisted of the following components in distilled water (g/L): potato starch, 5.0; pectin (citrus), 2.0; casein (sodium salt), 3.0; Raftiline LS (Orafti, Timm; BE), 1.0; xylan (oat hull), 2.0; arabinogalactan (Fluka), 2.0; guargam, 1.0; mucin (porcine gastric type III), 4.0; tryptone (Oxoid), 5.0; peptone water (Oxoid), 5.0; yeast extract (Oxoid), 4.5; bile salts No. 3 (Oxoid), 0.4; L-cysteine HCl, 0.8; NaHCO3 (Fisher Scientific), 1.5; hemin, 0.05; NaCl (Fisher Scientific), 4.5; KCl (Fisher Scientific), 4.5; CaCl2×6H2O (BDH), 0.15; KH2PO4 (BDH), 0.5; FeSO4×7H2O (BDH), 0.005; MgSO4×7H2O (Fisher Scientific), 1.25. In addition, 1.0 ml of Tween 80 (BDH) and 10 microliters of vitamin K were added. A 4 ml concentration of a 0.025% (w/v) solution of resazurin was added to the growth medium as indicator of anaerobic conditions. The medium was autoclaved at 121° C. for 15 min and cooled under a nitrogen atmosphere. Unless indicated otherwise, all chemicals were purchased from Sigma Chemical Co., UK.

Collection and Preparation of Fecal Material:

The remaining volume of each vessel was made up with freshly prepared fecal suspension from a 30-year old man who had not taken any antibiotics for three months before the test. The 20% (w/w) fresh fecal suspension was prepared with previously reduced phosphate-buffered saline (PBS) and digested at normal speed for 2 minutes in a digestion apparatus (stomach). Large food residues were removed through a filter sack. One hundred ml of the resulting suspension were then employed to inoculate each of the three fermentation vessels. The system was initially operated as batch culture using the culture medium over 48 hours. After 48 h of batch culture fermentation, the complex growth medium which simulates the composition of intestinal fluid was introduced into V1 and then into V2 and V3 via the peristaltic pump. The residence time (R) was calculated as reciprocal dilution rate for each vessel. The residence time was set at 27.1 hours, and the system was operated for 12 days after the initial 48 h equilibrium period to ensure a steady state. The overall residence time was the total of the individual residence times R of each fermenter.

Sampling:

The first sample (5 ml) (day 0) was taken after fermentation for 24 h. The fermentation continued until a steady state was reached (after 10-12 days) (SS1). At this stage, samples of the culture liquid were removed from each vessel for subsequent analysis of bacteria and short-chain fatty acids, and used as indicator of SS1. After SS1 was reached, the test substrate was put into vessel 1 each day for a further period of 10-12 days. The fermentation was continued until a further steady state (SS2) was reached and once again samples were taken of the culture liquid from each vessel for subsequent analysis.

Counting of bacteria in fecal samples and samples from the bowel model by FISH analysis:

Samples from individual vessels of the fermentation system were treated as shown below. Sample preparation: samples (375 μl) were removed from the batch cultures, added to 1125 μl of filtered 4% (w/v) paraformaldehyde solution (pH 7.2), mixed and stored at 4° C. overnight in order to fix the cells. The fixed cells were centrifuged at 13 000 rpm for 5 minutes and washed twice in filtered phosphate buffer solution and resuspended in 150 μl of PBS. Ethanol (150 μl) was added, and the sample was mixed and stored at −20° C. until used, but not for more than 3 months.

Hybridization:

The fixed cells (16 μl) were added to 264 μl of preheated (oven) filtered hybridization buffer (preheated in X (30 mM Tris-HCl, 1.36 M NaCl, pH 7.2, 0.1% v/v sodium dodecylsulfate, SDS) and mixed. The mixture was added to the suitable Cy3-labeled probe (50 ng/μl) in a ratio of 9:1 (v/v), mixed and placed in the hybridization oven at a suitable temperature overnight.

Washing and Filtering:

The hybridized sample (suitable aliquots to achieve from 30 to 150 cells per field of view) was added to 5 ml of preheated, filtered hybridization buffer (20 mM Tris-HCl, 0.9 M NaCl, pH 7.2) together with 20 μl of DAPI (4',6-diamidino-2-phenylindole, 500 ng/μl) and left at the suitable hybridization temperature for 30 min. The mixture was put on a black membrane filter with a pore size of 0.2 μm (GTBP 01300, Millipore Corp.). Slowfade-Light Antifade (Molecular Probes Europe, Leiden, NL) was put on the filter in order to prevent fading of the fluorescence, and the supports were stored in the dark at 4° C. for a maximum of 3 days.

A minimum of 15 fields of view per support was examined with a Nikon Microphot EPI fluorescence microscope (1000× magnification). The DM510 filter (550 nm) was used in order to count the hybridized cells, and the DM400 extraction filter was used for the DAPI-stained cells.

The following formula was used to calculate the concentration of cells C (cells/ml) in each sample:

$$C = N \times 15.56 \times 14\,873.74 \times (1000/q)$$

N: average number of cells counted per field of view
q: volume of hybridization mixture used
14 873.74: magnification constant
15.56: factor for all dilutions made Genus-specific 16S rRNA-targeted oligonucleotide probes labeled with the fluorescent dye Cy 3 which have previously been designed and validated were used to count important groups of bacteria. The probes used were Bif164, specific for *bifidobacterium* (Langedijk (1995), Appl Environ Microbiol 61, 3069-3075), Bac303, specific for *bacteroides* (Manz et al. (1996) Microbiology 142, 1097-1106), His150, specific for the *Clostridium histolyticum* subgroup and Erec482, specific for the *Clostridium coccoides-Eubacterium rectale* group (Franks et al. (1998) Appl Environ Microbiol 64, 3336-3345), Lab158, specific for *Lactobacillus/Enterococcus* (Harmsen et al. (1999) Microb Ecol Health Dis 11, 3-12), Ato291, specific for *Atopobium* cluster. The nucleic acid dye 4',6-diamidino-2-phenylindole (DAPI) was used for total cell counting (table 13)

Analysis of Short-Chain Fatty Acids:

Short-chain fatty acids (SCFA) in samples taken from various vessels of the bowel model were analyzed as described in Pereira et al., Appl. Environ Microbiol (2003) 69(8), 4743-4752. The samples were centrifuged (6000 g, 10 min) in order to remove bacteria and solids and then filtered through a polysulfone HPLC filter with a pore size of 0.2 μm. Then 200 μl of each filtered supernatant were diluted with 800 μl of acetonitrile (1:4) which contained 3.7 mM 2-ethylbutyric acid as internal standard. The fatty acids were determined by gas chromatography using a HP 5890 series II GC system provided with a fused silica packed capillary column (Permabond FFAP, Macherey Nagel, Del.) (25 m×0.32 mm, film thickness 0.25 μm). Helium was used as carrier gas with a volumetric flow of 2.42 ml/min. The column temperature was 140° C. and the injector and detector temperature was 240° C. 5 minutes after injection of the sample, the column temperature was increased in steps of 20° C./min to 240° C. and the system was left to run for a further 5 minutes. The gas composition was analyzed using an HP 3365 series II ChemStation Apg-top Software, Version A0.03.34. The following acids were used as external standards, each with concentrations in the range from 0.5 to 40 mM: acetic acid, propionic acid, n-butyric acid, n-valeric acid, isovaleric acid (Fluka), isobutyric acid (Fluka) and n-caproic acid. Unless indicated otherwise, all the acids were purchased from Sigma and were more than 99% pure. The SCFA concentrations were calculated using an internal standard calibration and expressed in mM per liter.

2. Results

The following inulins were tested in the bowel model described above:

Inulin of the invention: DPw=95
Comparison sample: Raftinline HP® (Orafti), DPw=33

Comparison was made between the second steady state (SS2) and the first steady state (SS1) and the data were analyzed using Student's t test.

Figure 6:
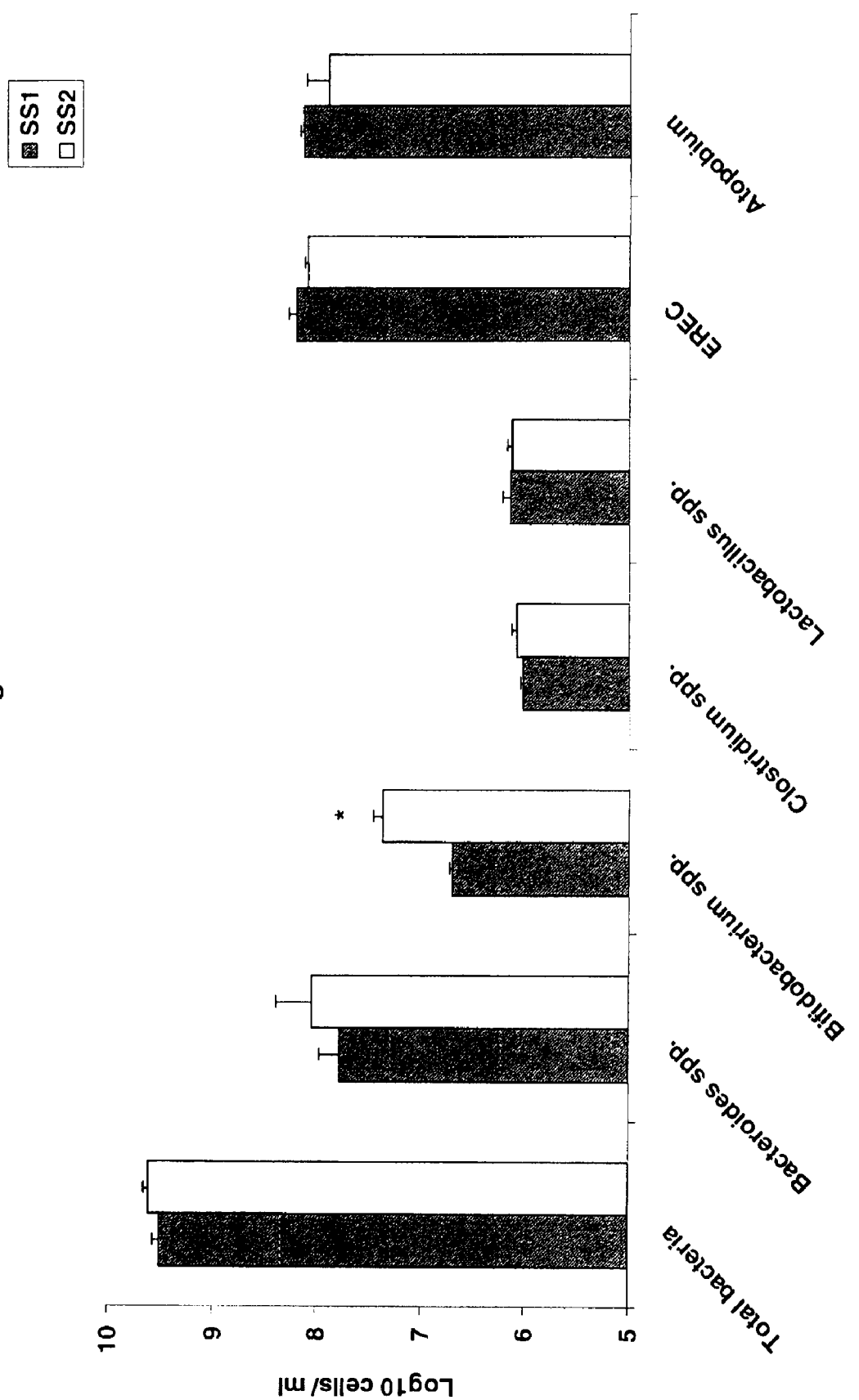
FIG. 6: shows the comparison of the bacterial population in vessel 1 (V1) between steady state 1 (SS1) and steady state 2 (SS2) after treatment with inulin of the invention.
Figure 7:
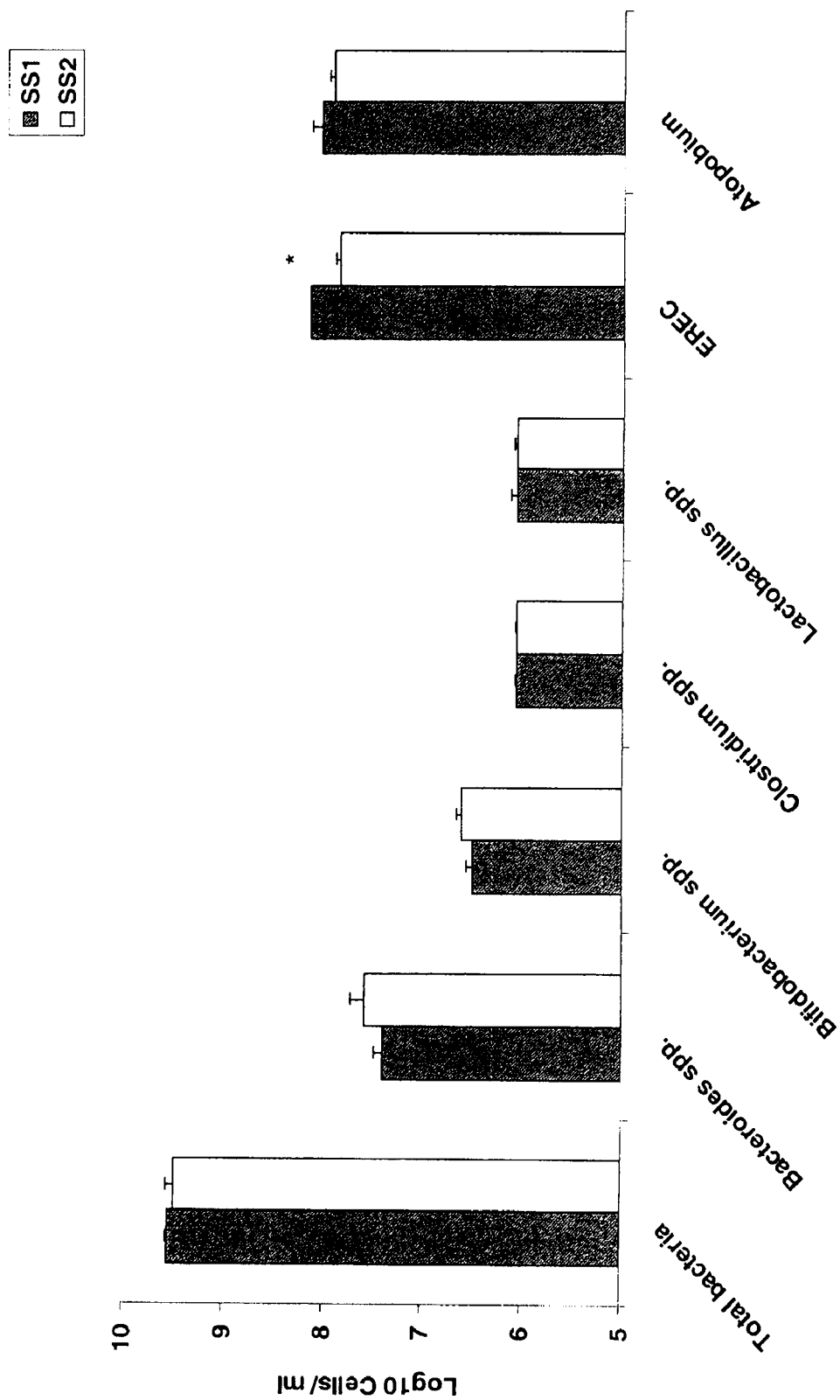
FIGS. 7 and 8 show corresponding comparisons for vessel 2 (V2) and 3 (V3).
Figure 8:
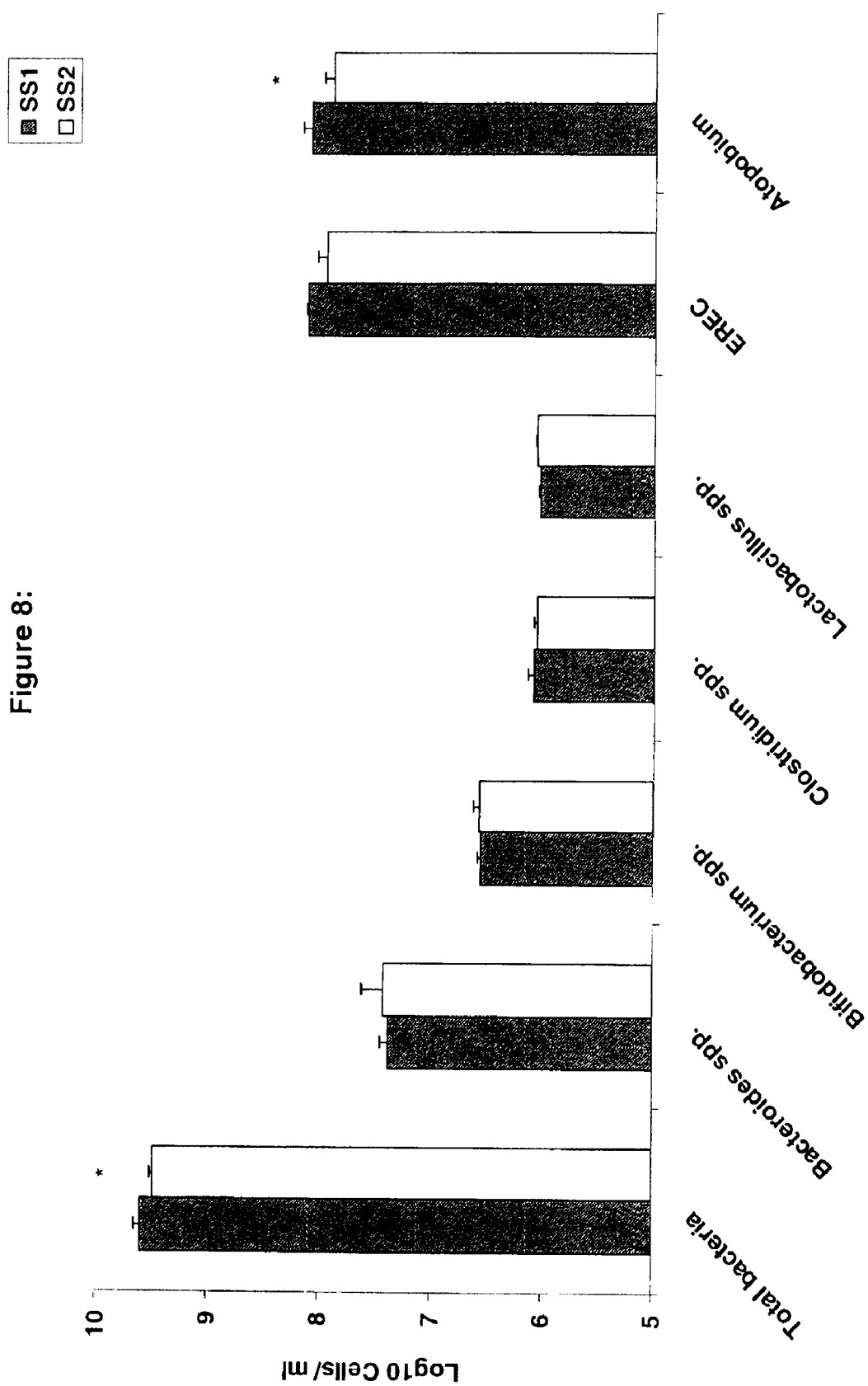

FIG. 6 shows the comparison of the bacterial population in vessel 1 (V1) between steady state 1 (SS1) and steady state 2 (SS2) after treatment with inulin of the invention. FIGS. 7 and 8 show corresponding comparisons for vessel 2 (V2) and 3 (V3).

Figure 9:
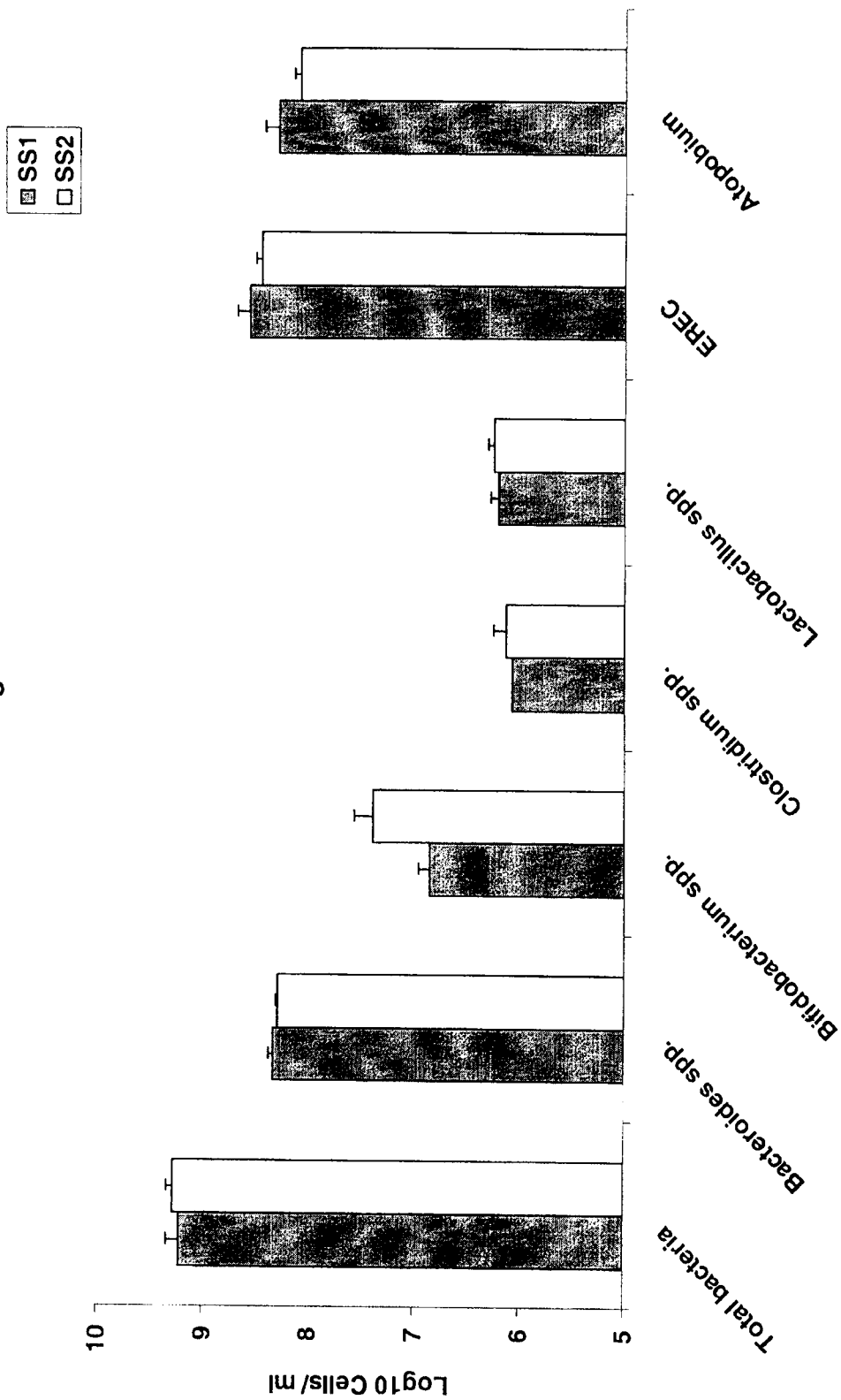
FIG. 9 shows the comparison of the bacterial population in vessel 1 (V1) between steady state 1 (SS1) and steady state 2 (SS2) after treatment with the comparative sample.
Figure 10:
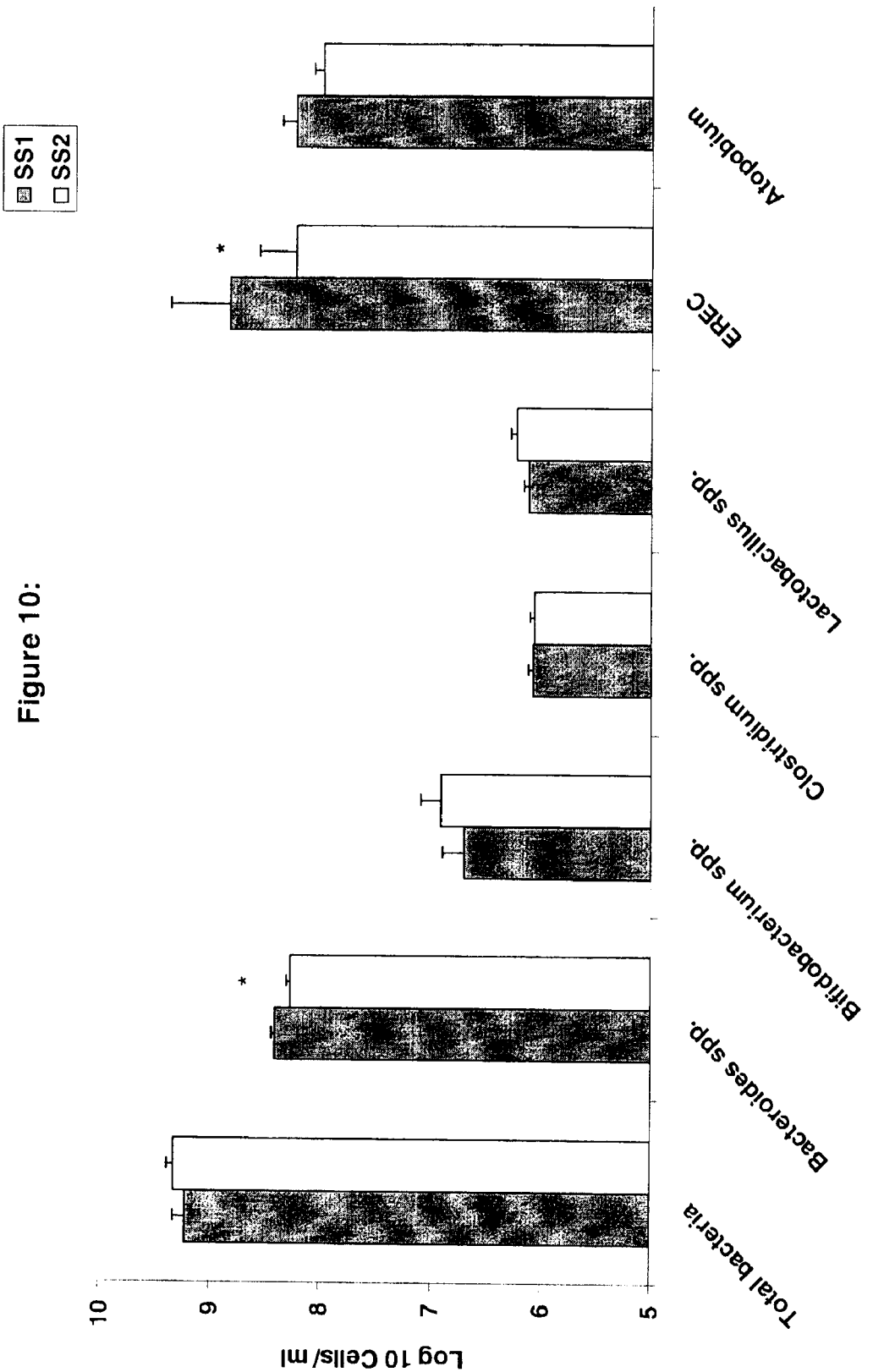
FIG. 10 and FIG. 11 show corresponding comparisons for vessel 2 (V2) and 3 (V3).
Figure 11:
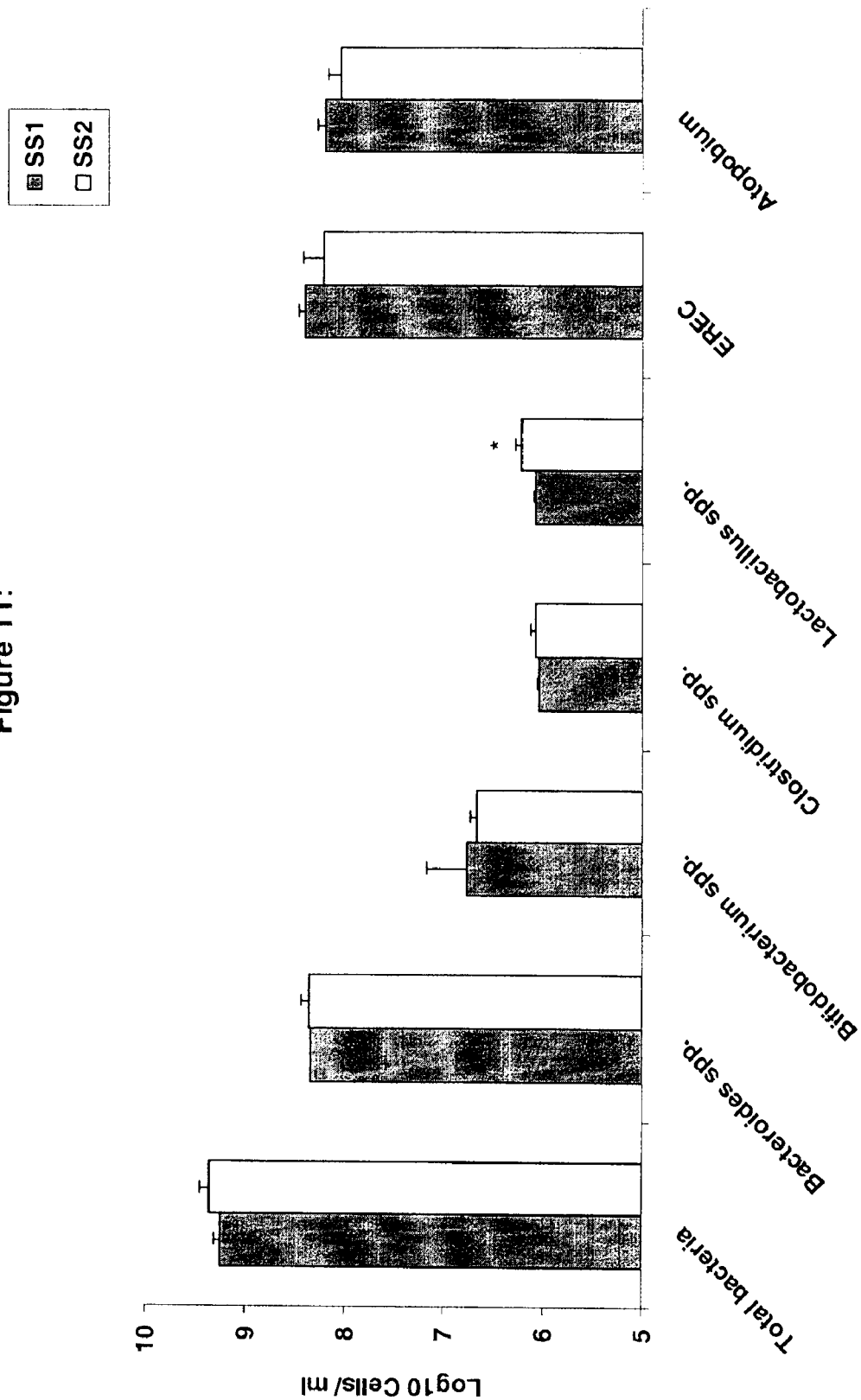

FIG. 9 shows the comparison of the bacterial population in vessel 1 (V1) between steady state 1 (SS1) and steady state 2 (SS2) after treatment with the comparative sample. FIGS. 10 and 11 show corresponding comparisons for vessel 2 (V2) and 3 (V3).

TABLE 13

| Probe | Target genus | Sequence (5' to 3') | T-hybridization/ ° C. |
|---|---|---|---|
| Bif 164 | *Bifidobacterium* spp. | CATCCGGCATTACCACCC | 50 |
| Bac 303 | *Bacteroides* spp. | CCAATGTGGGGGACCTT | 45 |
| Chis 150 | *Clostridium histolyticum* group | TTTCCYTCTAATTATGGCGTATT | 50 |
| Lab 158 | *Lactobacillus/Enterococcus* spp. | GGTATTAGCATCTGTTTCCA | 50 |
| Ato 291 | *Atopobium* cluster | GGTCGGTCTCTCAACCC | 50 |
| Erec 482 | *Clostridium coccoides-E. rectale* group | GCTTCTTAGTCARGTACCG | 52 |

Addition of the inulin of the invention in the bowel model led to a significant increase in bifidobacteria in vessel 1 (P<0.05). A non-significant increase was observed in the other vessels. An increase in bifidobacteria in vessel 1 was observed, but was not significant, with the comparative sample. The population of lactobacillae in vessel 3 was significantly higher (P<0.05), but no change was observed in the population of Clostridia. *Bacteroides* and the *Clostridium coccoides-E. rectale* group was significantly lower in vessel 2 (P<0.05).

Figure 12:
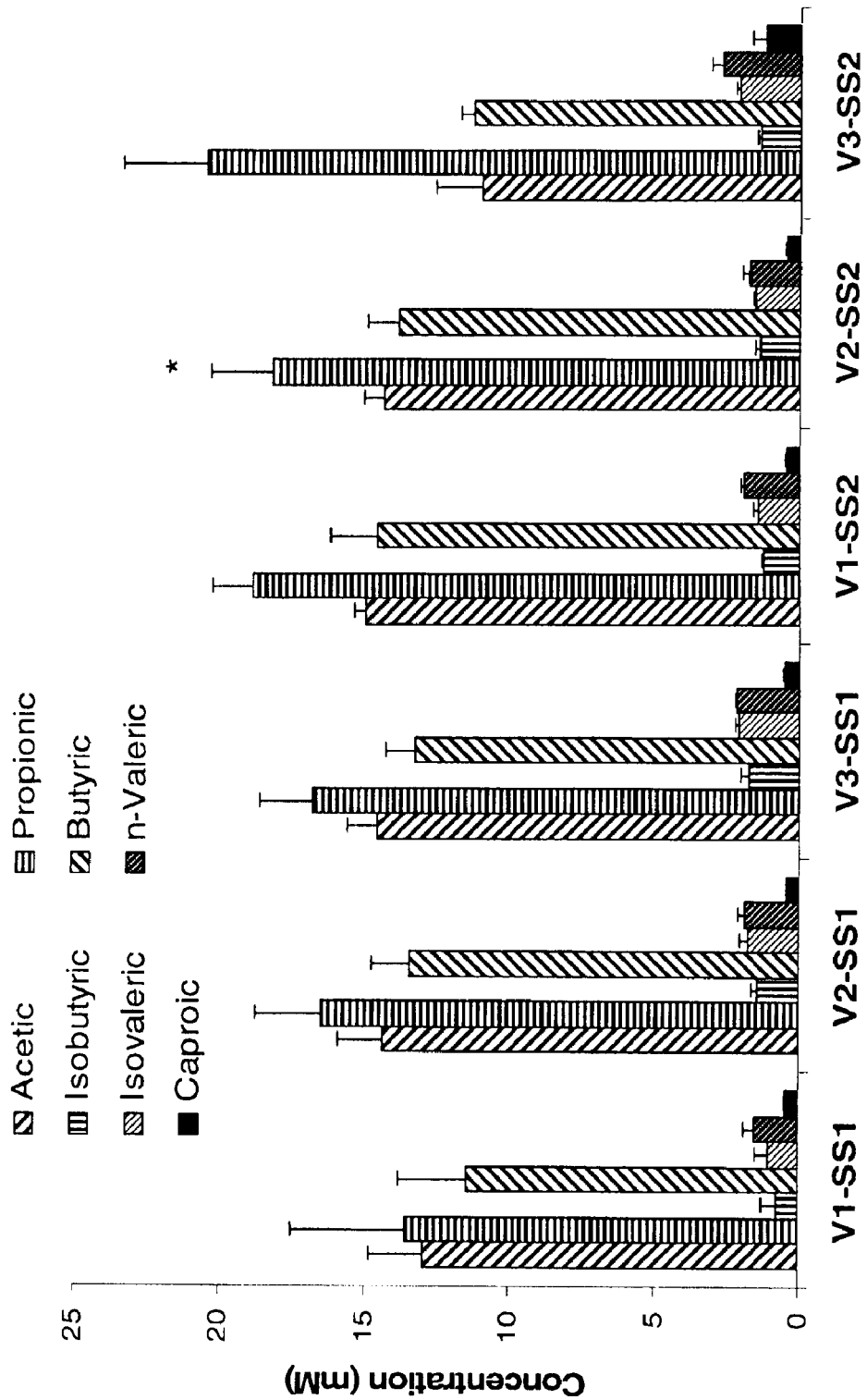
FIG. 12 shows a comparison of the concentration of short-chain fatty acids (SCFA) in all vessels between steady state 1 (base line) (SS1) and steady state 2 (SS2) after treatment with inulin of the invention.

FIG. 12 shows a comparison of the concentration of short-chain fatty acids (SCFA) in all vessels between steady state 1 (base line) (SS1) and steady state 2 (SS2) after treatment with inulin of the invention. The individual fatty acids are plotted in each case as bile diagram for each vessel and steady state (e.g. V1-SS1). From left to right: acetic acid, propionic acid, isobutyric acid, butyric acid, isovaleric acid, n-valeric acid, caproic acid.

Figure 13:
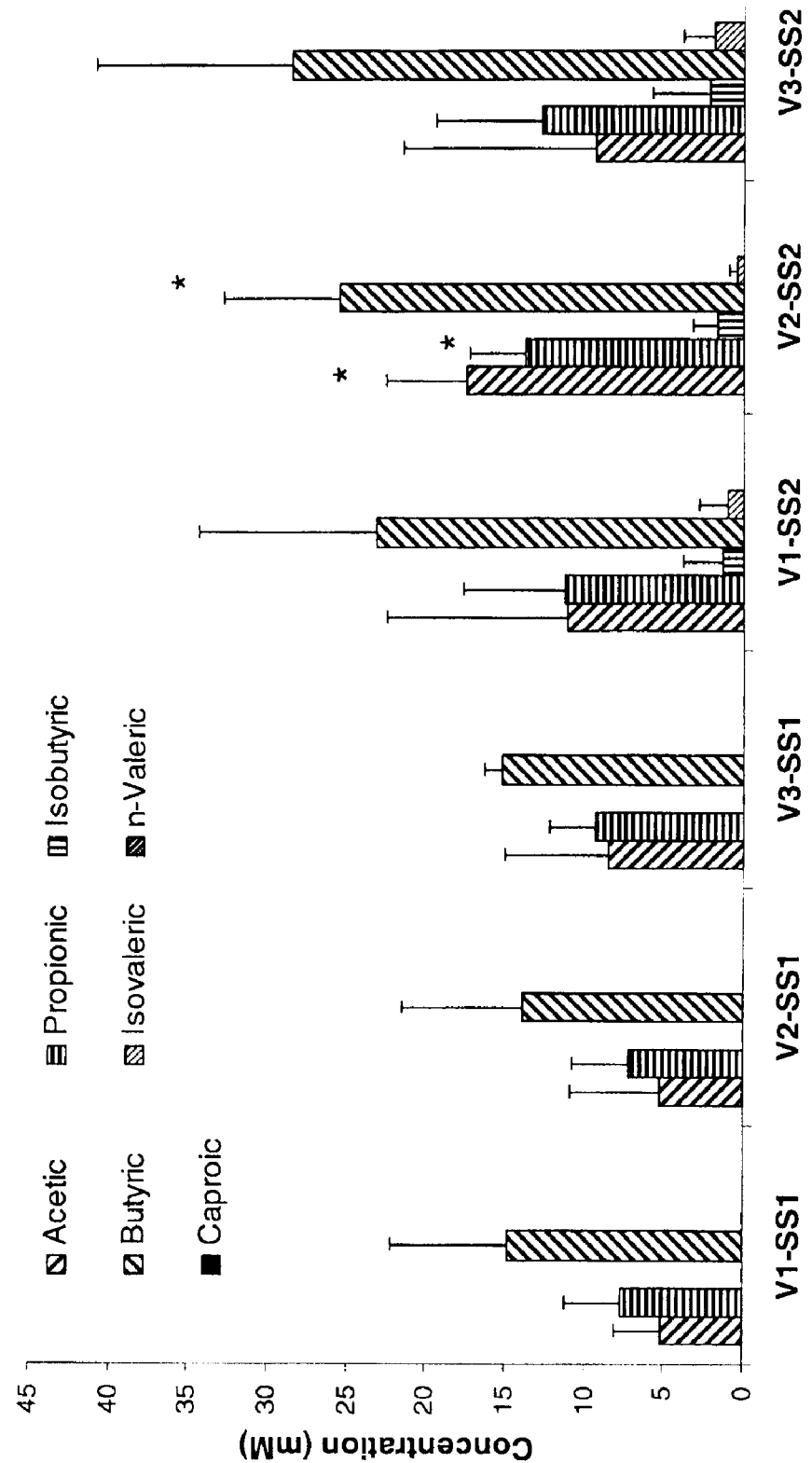
FIG. 13 shows the comparison of the concentration of short-chain fatty acid (SCFA) in all vessels between steady state 1 (base line) (SS1) and steady state 2 (SS2) after treatment with the comparative sample.

FIG. 13 shows the comparison of the concentration of short-chain fatty acids (SCFA) in all vessels between steady state 1 (base line) (SS1) and steady state 2 (SS2) after treatment with the comparative sample.

There was an increase in the propionic concentration in all three vessels after addition of inulin of the invention, and the increase in vessel 2 was significant. The butyrate concentration increased in vessels 1 and 2. Addition of the comparative sample to the bowel model led to an increase in the concentration of acetate, propionate and butyrate in all vessels, but this was significant only in vessel 2.

8. Dough and Baking Properties

Material

The material used for the baking tests comprised flour blends composed of the American wheat flour "King Midas"® plus Raftiline HP® supplied by Orafti or inulin of the invention with DPw=86.8% of the flour was replaced by inulin. The blended flour and the control without replacement were then subjected to measurements of dough rheology and baking tests.

Methods:

1) Farinogram (Complying with ICC and AACC Standard):

The farinogram is used to ascertain the water-uptake capacity of the flour and to assess the kneading properties of the prepared dough.

Reagents: dist. water

Equipment:

Farinograph® E with USB port supplied by Brabender, Germany 10 g kneader with 2 kneading blades (Brabender)

The following parameters were determined and evaluated for the quality characteristics of the tested flour:

Water uptake of the flour: defined as the amount of water in ml required per 100 g of flour with 14% moisture content when the dough has reached a maximum dough consistency of 500 FU (Farinograph units).

The dough consistency is the resistance of the dough at constant revolutions (63 rpm), which is stated in FU.

The dough development time is defined as the time in min between the start of the test (addition of water) and the maximum peak.

2) Baking Test (White Pan Bread):

Equipment
    Farinograph with 300 g flour-kneading chamber supplied by Brabender, Germany
    Baking oven (MIWE gusto, Germany)
    Fully automatic fermenter (Foster RBC Mk3, from Hobart, Germany)
    2 kg weighing machine (Sartorius)
    Kneader (Brabender, Germany)

Ingredients for the Dough:

300 g of flour (with 14% flour moisture)

12 g of yeast (fresh)

6 g of salt (table salt)

15 g of baking fat 3 g of sugar

Water (equivalent to the water uptake less 2.5%)

Dough Processing:

The flours and ingredients were mixed in the kneading chamber for 1 min and then the appropriate amount of water was added. After kneading for 2 min, the equipment was switched off in order to return the dough from the wall of the kneading chamber to the mass of dough. The kneading process was continued for 6 min or 12 min for the inulin-supplemented flours, according to the farinogram data (dough development time in min). The final temperature of the doughs was about 26° C. After completion of the kneading, the dough was left to stand for 10 min and then the total weight of dough was determined. The dividing and measuring of the weight of the pieces of dough took place within 10 min. The dough was divided into two pieces of dough of equal size and kneaded round in the kneader (Brabender) for 10 s and then rolled into oblongs. The pieces of dough were placed in the bread-baking molds and pushed into the fully automatic fermenter (32° C., humidity 87%) for 60 min (fermentation time). The baking oven was preheated to 250° C. The fermented pieces of dough were sprayed with water and pushed into the baking oven. After a baking time of 30 min at about 200° C., the loaves were removed and left to cool at room temperature for 1 hour. The bread volume was measured by the displacement of rapeseeds. The crumb properties were investigated visually and using the TA-TX2 texture analyzer (Stable Micro Systems). The crumb strength was measured on pieces of bread about 1.5 cm thick using the SMSP/0.5 R076 penetration punch (Stable Micro Systems) with a diameter of 12 mm. The following parameters were used in the TA measurement with the 5 kg measuring cell. The measurement took place after the following adjustment:

Options: measure force in direction of pressure
    Single test
    Parameter: forward speed 2.00 mm/s
    Test speed 0.50 mm/s
    Reverse speed 0.50 mm/s
    Travel (depth of penetration) 7 mm
    Trigger force 2 g Results:

DEFINITION OF TERMS

Dough yield (DY): is the amount of dough from 100 parts by weight of flour. It is a characteristic making it possible to compare the water-uptake capacity and dough strengths of flours. A dough made from 100 kg of four and 60 kg of water with a DY of 160 is an example. The dough yield has various definitions:

Nett dough yield: is the amount of dough from 100 parts by weight of flour and the water
    Gross dough yield: is the amount of dough from 100 parts by weight of flour, the water and the other ingredients
    Practical dough yield: is the gross dough yield taking account of processing, fermentation and weighing losses.
    Baking loss: the baking loss is understood by the skilled worker to be the loss in weight of the dough or the pieces of dough during the baking. This is chiefly composed of water evaporated from the dough, and minimal amounts of other volatile constituents such as alcohol, organic acids and esters; the skilled worker therefore also speaks of "water loss" in the same way.

The weight loss (=baking loss) is always based on the dough weight and represents the ratio of dough weight to bread weight. It is calculated as follows:

$$\text{Baking loss} = \frac{\text{dough weight} - \text{bread weight}}{\text{dough weight}} \times 100$$

High baking losses have disadvantageous effects on the baker's product yield and thus on the weight and number of baked products to be sold. In addition, the water losses during the baking process have disadvantageous effects on the freshness of the baked products, which thus become old, i.e. "stale", sooner.

Product Yield (Also Bread Yield):

The bread yield (BY) is the amount of baked product obtained from 100 parts of flour. The bread yield is based on the amount of flour processed.

Example: 40 kg of flour result in 60 kg of bread and a BY of 150.

TABLE 14

Farinogram data

| Parameter | Control | Control + 8% Raftiline HP ® | Control + 8% Inulin DPw = 86 |
|---|---|---|---|
| Flour moisture (%) | 12.7 | 12.2 | 12 |
| Water uptake (%) | 63.3 | 57.7 | 66.3 |
| Dough development time (min) | 8 | 12.7 | 8.7 |

TABLE 15

Baking results

| Parameter | Control | Control + 8% Raftiline HP ® | Control + 8% Inulin DPw = 86 |
|---|---|---|---|
| Net dough yield (%) | 161 | 155 | 164 |
| Gross dough yield (%) | 171 | 164 | 174 |
| Dough consistency | normal | slightly sticky | normal |
| Bread yield (%) | 147.6 | 143 | 147.9 |
| Baking loss (%) | 13.7 | 13.9 | 14.7 |
| Bread volume (ml/100 $g_{flour}$) | 616 | 513 | 541 |
| Specific bread volume (ml/$g_{bread}$) | 4.2 | 3.6 | 3.7 |
| Bread crumb: | | | |
| Color | white | white | white |
| Elasticity | good | satisfactory | good |
| Porosity | uniform | uniform | uniform |
| Looseness | somewhat coarse | delicate | woolly |
| Crumb strength (g): | | | |
| Fresh | 73 | 132 | 82 |
| 3 days | 181 | 221 | 165 |
| 7 days | 222 | 318 | 211 |
| Water content (%): | | | |
| Fresh | 43.2 | 40.4 | 44 |
| 3 days | 43.2 | 40.6 | 42.4 |
| 7 days | 41.8 | 37.6 | 43.4 |
| Browning | normal | somewhat strong | somewhat strong |

The investigation of the dough rheology revealed a distinct increase in water-uptake capacity of the dough with replacement by the inulin of the invention (table 14). It is almost 9 percent higher than that of the comparative flour which contains Raftiline HP and is still 3% higher than that of the comparative flour in which no replacement was made. The dough yield, which is of particular commercial interest, is consequently clearly highest for the dough containing the inulin of the invention (table 15). This is surprising because the dough to which Raftiline HP® was added shows a great reduction in the dough yield compared with the control dough. The consistency of the dough with inulin of the invention is also advantageous by comparison with the dough with Raftiline HP®. The bread yield is highest for the bread with inulin of the invention, whereas it is lowest for the bread containing Raftiline HP®. The specific volume of the two breads in which there was replacement of flour is similar, while the other quality parameters such as crumb color, elasticity, porosity or looseness are somewhat better for the bread with inulin of the invention than for the comparative bread with Raftiline HP® and the control without replacement. The bread containing inulin of the invention shows a particular advantage in relation to maintenance of freshness. This is improved as shown by the crumb strength compared with the control bread and the Raftiline HP-containing bread. A further advantageous property is also the increased water content of the fresh and stored crumb, which is associated in particular with sensory improvement besides a reduced aging.

3) Pasta Production:

An further application of the inulin samples was tested in pasta production. In this case, 5% and 10% of the wheat meal were replaced by inulin.

1) Material:

Durum wheat meal
Inulin of the invention with DPw=86
Raftiline HP®

2) Preparation of the Pasta Dough:

The pasta dough was prepared by using 200 g of meal-inulin mixture with addition of 34.5 or 35% water. The control dough (wheat meal without replacement) was prepared with addition of 34% water. Since the doughs with inulin were slightly drier than those of the control, the addition of water was consequently increased. The pasta doughs were prepared using the "Luna" pasta machine from HÄUSSLER. The dough-making time was 5 min. Broad pasta was produced using a die with a width of 9.5 mm.

3) Method:

One part of the freshly extruded pasta strips was, immediately after leaving the machine, treated with 3 different cooking times. The second part was left to dry in the air under ambient conditions for 2 days. For the cooking test, in each case 3 pasta strips (fresh) were weighed and passed into a falcon (50 ml) charged with 45 ml of boiling water. The pasta was boiled at about 100° C. for 2, 3 or 5 min and then allowed to drain on a sieve for a constant time. The weights of the cooked pasta strips were then determined. The swelling of the pasta was determined from the weights of the pasta strips before and after cooking.

The pasta strips which had dried for 2 days were likewise cooked, but for times of 5, 10 and 15 min. In these cases, the swelling index of the pasta was also determined.

The following formula was used to calculate the swelling index:

Swelling index=(weight after cooking/weight before cooking)

4) Result:

The increased addition of water to prepare the pasta dough with supplemented inulin correspondingly increased the yield of pasta dough. The increase in the yield is advantageous in commercial respects. It can also be established from the cooking test that the pasta with supplemented inulin of the invention should distinctly increase the swelling compared with the control and also with the pasta supplemented with Raftiline HP®. This increase is between 5 and 20% (see table 16).

TABLE 16

| Inulin content | Raftiline | % vs control | Inulin DPw = 86 | % vs control |
|---|---|---|---|---|
| None | 2.06 | | 2.09 | |
| 5% 5 min | 2.08 | 101 | 2.18 | 105 |
| 10% 5 min | 2.09 | 101 | 2.38 | 114 |
| None | 2.7 | | 2.68 | |
| 5% 10 min | 2.73 | 101 | 2.9 | 108 |
| 10% 10 min | 2.93 | 109 | 3.09 | 115 |
| None | 3.25 | | 3.06 | |
| 5% 15 min | 3.28 | 101 | 3.42 | 112 |
| 10% 15 min | 3.38 | 104 | 3.70 | 121 |

9. Production of Yogurt

The yogurt recipes are listed in table 17. The inulin of the invention (very long chain inulin, VLCI) corresponded to inulin from example 1/table 2, was spray dried under the conditions of table 9, test 2, and had an average degree of polymerization DPw of 86; the comparative sample Beneo HP® had a DPw of 34. All percentages relate to percent by weight based on the total composition, unless indicated otherwise.

The dry ingredients were mixed together in order to facilitate the dispersion of inulin and fat-free dry milk, and then added to the milk with moderate shearing in order to form the yogurt base. The standardized base was maintained at 4° C. for 3 hours so that the fat-free dry milk could dissolve completely. Each batch was pasteurized at 80° C. for 30 minutes, rapidly cooled to 44° C. and inoculated with Yo-Flex 88 (*Streptococcus thermophilus* and *Lactobacillus delbrueckii*, from Chr. Hansen Inc.) in a concentration of 3.6 g/l. For pot-fermented yogurt (custard style yogurt), inoculated base was poured into the final packs before incubation. The base mixes were incubated at 44° C. for 4-6 hours until they reached pH 4.5 (initial pH about 6.8). When the yoghurt reached pH 4.5, the custard-style yogurt samples were cooled to 4° C. and maintained thereat for 48 hours in order to reach the maximum viscosity. The viscosity was measured with a Brookfield viscometer with a heliopath adapter.

Table 17 shows the results with pod-fermented yogurt (custard style). 2.5% spray-dried inulin of the invention bring about a greater increase in viscosity than 4.5% inulin from the comparative example. The yogurt with inulin of the invention also has a higher viscosity than a comparative yogurt with a high fat goods content of 3.35%.

TABLE 17

| | Comparative example 4.5% commercial inulin | Example 2.5% inulin spray dried | Comparative example 1.5% fat | Comparative example 3.35% fat |
|---|---|---|---|---|
| a) Data on the individual ingredients | | | | |
| Whole milk | — | — | — | 95.91 |
| 2% milk | — | — | 71.85 | — |
| Sugar | — | — | — | — |
| Skimmed milk | 91.51 | 93.44 | 24.06 | — |
| Fat-free dry milk | 3.21 | 3.28 | 3.37 | 3.37 |
| Stabilizer CC723 | 0.69 | 0.70 | 0.72 | 0.72 |
| Beneo HPX ® | 4.59 | — | — | — |
| Inulin DPw = 86 spray dried | — | 2.58 | — | — |
| b) Data on the solids | | | | |
| Milk solids | 11.14 | 11.37 | 11.67 | 11.67 |
| Inulin | 4.59 | 2.58 | — | — |
| Fat | — | — | 1.44 | 3.36 |
| Total solids | 15.73 | 13.95 | 13.11 | 15.03 |
| Viscosity (centipoise) | 302500 | 335000 | 281250 | 320000 |
| pH | 4.34 | 4.45 | 4.57 | 4.55 |

All data in percent based on the total mass, excepting viscosity and pH

---

The invention claimed is:

1. Inulin having a weight average degree of polymerization $DP_W$ of between 83 and 103, wherein said inulin is spray-dried.

2. The inulin of claim 1, wherein said inulin has a weight average degree of polymerization $DP_W$ of between 85 and 95.

3. The inulin of claim 1, wherein said inulin has a degree of branching of between 0.5 and 2.0 mol % of 2-1,6 linked fructose monomers based on all inulin monomers.

4. The inulin of claim 1, wherein the quotient between the weight average degree of polymerization and the number average degree of polymerization (DPw/DPn) of said inulin is less than 1.25.

5. The inulin of claim 1, wherein the quotient DPw/DPn of said inulin is less than 1.20.

6. The inulin of claim 1, wherein the quotient DPw/DPn of said inulin is less than 1.15.

7. The inulin of claim 1, wherein said inulin has a glucose content less than 2% by weight based on the total dry weight.

8. The inulin of claim 1, wherein said inulin has a glucose content less than 1% by weight based on the total dry weight.

9. The inulin of claim 1, wherein said inulin has a fructose content less than 2.5% by weight based on the total dry weight.

10. The inulin of claim 1, wherein said inulin has a fructose content less than 1.5% by weight based on the total dry weight.

11. The inulin of claim 1, wherein said inulin has a weight average degree of polymerization $DP_W$ of between 85 and 95.

12. The inulin of claim 1, wherein said inulin is in the form of particles with an average diameter of 100-250 μm.

13. A process for obtaining inulin comprising
  a) comminuting artichoke roots,
  b) obtaining an extract by treating the comminuted roots with water,
  c) removing coloring constituents from the extract,
  d) precipitating inulin from the extract,
  e) reprecipitating the inulin at least once,
  f) dissolving and filtering the inulin obtained in step e), and
  g) precipitating and separating the inulin obtained in step f),
wherein said inulin has a weight average degree of polymerization $DP_W$ of between 83 and 103.

14. The process as claimed in claim 13, further comprising an additional filtration step.

15. The process as claimed in claim 13 wherein the coloring constituents are removed in step c) by
  i) admixing magnesium ions ($Mg^{2+}$) to the plant extract,
  ii) admixing at least one alkaline component to the plant extract,
  iii) forming a precipitate, and
  iv) removing the precipitate which has formed from the plant extract.

16. The process as claimed in claim 15, further comprising admixing a magnesium salt in step i).

17. The process as claimed in claim 16, wherein the magnesium salt is magnesium chloride, magnesium sulfate, magnesium nitrate, magnesium acetate, or magnesium propionate.

18. The process as claimed in claim 15, wherein step i) is carried out at a temperature of 60-80° C.

19. The process as claimed in claim 15, wherein the amount of alkaline component is chosen so that the $OH^-:Mg^{2+}$ molar ratio set up is 2.2:1-1.8:1.

20. The process as claimed in claim 15, wherein the alkaline component is an aqueous solution or suspension of an alkali metal hydroxide or alkaline earth metal hydroxide.

21. The process as claimed in claim 15, wherein the alkaline component is a suspension of calcium hydroxide.

22. A foodstuff comprising inulin having an average degree of polymerization $DP_W$ of between 83 and 103.

23. The foodstuff as claimed in claim 22, wherein said foodstuff is a dairy product, yoghurt, ice cream, milk-based soft ice, milk-based garnish, pudding, milkshake, egg custard, cheese, nutrition bar, energy bar, breakfast bar, confectionery, bakery product, cracker, cookie, biscuit, cereal chip, snack product, ice tea, soft ice made from fruit juice, diet drink, finished drink, sports drink, stamina drink, powdered drink mixture for dietary supplementation, infant and baby food, calcium-supplemented orange juice, bread, croissant, breakfast cereal, noodle, spread, sugar-free biscuit, sugar-free chocolate, calcium chew, meat product, mayonnaise, salad dressing, nut butter, deep-frozen meal, sauce, soup or ready-to-serve meal.

24. The foodstuff as claimed in claim 22, wherein said foodstuff is an extrusion product.

25. A dietary supplement comprising inulin having an average degree of polymerization $DP_W$ of between 83 and 103.

26. A cosmetic preparation comprising inulin having an average degree of polymerization $DP_W$ of between 83 and 103.

27. A method for manufacture of a foodstuff comprising adding inulin having an average degree of polymerization $DP_W$ of between 83 and 103 to a foodstuff.

28. The method as claimed in claim 27, wherein said inulin acts as an additive with prebiotic properties, a texturizing agent, a stability enhancing agent, a viscosity-building agent, and/or a dietary fiber in said foodstuff.

29. A method of making a foodstuff comprising inulin having an average degree of polymerization $DP_W$ of between 83 and 103 comprising adding inulin to a food stuff, wherein said inulin acts as a fat or oil substitute in said foodstuff.

30. A method for manufacture of a cosmetic preparation comprising adding inulin having an average degree of polymerization $DP_W$ of between 83 and 103 to a cosmetic preparation.

31. The method as claimed in claim 30, wherein said inulin acts as a texturizing agent, a stability enhancing agent, and/or a viscosity-building agent in said cosmetic preparation.

32. An aqueous paste comprising the inulin having an average degree of polymerization $DP_W$ of between 83 and 103.

33. A method for the manufacture of a foodstuff or a cosmetic preparation comprising adding the aqueous paste as claimed in claim 32, wherein the inulin in the aqueous paste acts as a structure imparting component, a fat substitute, an oil substitute, a texturizing agent, a stability enhancing agent, and/or a viscosity-building agent in said foodstuff or cosmetic preparation.

34. The process as claimed in claim 13, further comprising spray drying said inulin.

35. The foodstuff as claimed in claim 22, wherein said inulin is spray-dried.

36. The dietary supplement as claimed in claim 25, wherein said inulin is spray-dried.

37. The cosmetic preparation as claimed in claim 26, wherein said inulin is spray-dried.

38. The method as claimed in claim 27, wherein said inulin is spray-dried.

39. The method as claimed in claim 29, wherein said inulin is spray-dried.

40. The method as claimed in claim 30, wherein said inulin is spray-dried.

41. The aqueous paste as claimed in claim 32, wherein said inulin is spray-dried.

* * * * *